United States Patent
Bruhns et al.

(10) Patent No.: US 7,248,925 B2
(45) Date of Patent: Jul. 24, 2007

(54) SYSTEM AND METHOD FOR DETERMINING OPTIMAL ATRIOVENTRICULAR DELAY BASED ON INTRINSIC CONDUCTION DELAYS

(75) Inventors: Ken Bruhns, Hackensack, NJ (US);
Xiaoyi Min, Thousand Oaks, CA (US);
Paul A. Levine, Santa Clarita, CA (US);
Euljoon Park, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 200 days.

(21) Appl. No.: 10/928,586

(22) Filed: Aug. 27, 2004

(65) Prior Publication Data
US 2006/0047319 A1    Mar. 2, 2006

(51) Int. Cl.
*A61N 1/36* (2006.01)
(52) U.S. Cl. ...................................... 607/25
(58) Field of Classification Search ............ 607/9, 607/17–18, 25, 30, 32, 59–60; 600/508–509
See application file for complete search history.

(56) References Cited

U.S. PATENT DOCUMENTS

| | | | |
|---|---|---|---|
| 4,108,148 A * | 8/1978 | Cannon, III .................. 607/9 |
| 4,603,705 A | 8/1986 | Speicher et al. ............. 128/786 |
| 5,179,949 A * | 1/1993 | Chirife ......................... 607/9 |
| 5,507,782 A * | 4/1996 | Kieval et al. .................. 607/9 |
| 5,540,727 A | 7/1996 | Tockman et al. ............ 607/18 |
| 6,650,931 B1 | 11/2003 | McClure et al. ............. 600/510 |
| 2002/0091333 A1 | 7/2002 | Hsu et al. .................... 600/518 |
| 2002/0151934 A1 | 10/2002 | Levine .......................... 607/9 |
| 2002/0151935 A1 | 10/2002 | Levine .......................... 607/9 |
| 2003/0014084 A1 | 1/2003 | VanHout ....................... 607/9 |
| 2003/0032991 A1* | 2/2003 | Poore .......................... 607/32 |
| 2003/0060850 A1 | 3/2003 | Zhu et al. ..................... 607/9 |
| 2003/0083700 A1 | 5/2003 | Hill ............................. 607/9 |
| 2003/0199928 A1 | 10/2003 | Hsu et al. ..................... 607/5 |
| 2004/0147966 A1 | 7/2004 | Ding et al. ................... 607/9 |
| 2005/0137630 A1 | 6/2005 | Ding et al. ................... 607/9 |

FOREIGN PATENT DOCUMENTS

EP    0 494 487 B1    7/1992

OTHER PUBLICATIONS

Yu et al., "Optimization of AV Delay in DDD Mode of Cardiac Resynchronization Therapy for Heart Failure Patients," *EUROPACE Supplements*, vol. 4 (Dec. 2003), A30-6.

(Continued)

*Primary Examiner*—Carl Layno
*Assistant Examiner*—Jessica L. Reidel

(57) ABSTRACT

A system and method for estimating optimal atrioventricular delay values for use in pacing the ventricles. Both the intrinsic inter-atrial conduction delay and the intrinsic atrioventricular conduction delay are determined for the patient and then the preferred atrioventricular pacing delay is derived therefrom. By taking into account intrinsic inter-atrial delay along with intrinsic atrioventricular delay, a more reliable estimate of the true optimal atrioventricular delay values for the patient can be achieved than with techniques that only take into account intrinsic atrioventricular delay values. In one example, the technique uses intracardiac electrogram (IEGM) signals and surface electrocardiogram (EKG) signals and hence can be performed by an external programmer without requiring Doppler echocardiography or other cardiac performance monitoring techniques. In another example, wherein the implanted device is equipped with a coronary sinus lead, the technique uses only IEGM signals and hence can be performed by the device itself.

12 Claims, 12 Drawing Sheets

OTHER PUBLICATIONS

Strohmer B. et al., "Evaluation of Atrial Conduction Time at Various Sites of Right Atrial Pacing and Influence on Atrioventricular Delay Optimization by Surface Electrocardiography," *PACE*, vol. 27 (Apr. 2004), pp. 468-474.

Strohmer B. et al., "AV-Delay Optimization Guided by Surface ECG: Impact on Stroke Volume in DDD Pacing," *EUROPACE* 2003.

Strohmer et al., "Validation of Total Atrial Conduction Time by Surface-ECG at Various Right Atrial Pacing Sites," *EUROPACE* 2003.

Koglek W. et al., "A Simple Method for AV-Delay Determination in Dual Chamber Pacemakers," *Herzschrittmachertherapie und Elektrophysiologie* (Herzschrittmacherther. Elektrophysiol.)(Germany) 2000, 11/4 (244-253). (pp. 1-16 provided in English).

Levine, P., MD, FACC, "Programming the AV Delay; Supplement A" *Guidelines to the Routing Evaluation, Programming and Follow-Up of the Patient with an Implanted Dual-Chamber Rate Modulated Pacing System* 2003.

Raúl Chirife et al., "Automatic Beat-to-Beat Left Heart AV Normalization: Is It Possible?," *PACE*, Novem 2003; vol. 26, pp. 2103-2110.

* cited by examiner

SYSTEM AND METHOD FOR DETERMINING OPTIMAL ATRIOVENTRICULAR DELAY BASED ON INTRINSIC CONDUCTION DELAYS

FIELD OF THE INVENTION

The invention generally relates to implantable cardiac stimulation devices for use in pacing the heart of a patient and in particular to techniques for determining optimal atrioventricular delay times for individual patients.

BACKGROUND OF THE INVENTION

Implantable cardiac stimulation devices, particularly pacemakers and implantable cardioverter defibrillators (ICDs), are usually configured to be used in conjunction with an external programmer that enables a physician to program the operation of an implanted device to, for example, control the specific parameters by which the pacemaker detects arrhythmia conditions and responds thereto. For instance, the physician may specify the sensitivity with which the pacemaker or ICD senses electrical signals within the heart and also specify the amount of electrical energy to be employed in pacing pulses or defibrillation shocks. Another common control parameter is the A-VP delay, which for dual chamber devices specifies the time delay between a paced or sensed (i.e. native) atrial event and a paced ventricular event. Additionally, the external programmer may be configured to receive and display a wide variety of diagnostic information detected by the implantable device, such as intracardiac electrogram (IEGM) signals sensed by the device, as well as diagnostic data from other sources, such as surface electrocardiogram (EKG) devices.

Herein, "A" is generally used to refer to atrial events, whether paced or sensed. "V" is used to generally refer to ventricular events, whether paced or sensed. In circumstances where it is necessary to distinguish between paced and sensed events, an "S" or "P" is appended. Hence, AS refers to a sensed atrial event, whereas AP refers to paced atrial event. VS refers to a sensed ventricular event, whereas VP refers to a paced ventricular event. A-VP represents the delay between either a paced or sensed atrial event, and a paced ventricular event. In addition, where appropriate, an "L" or "R" subscript is employed to distinguish between the left and right chambers of the heart. For example, $AP_R$ refers to a paced event in the right atrium. $VS_R$ refers to a sensed event in the right ventricle. Hence, $AP_R$-$VS_R$ represents the delay between a paced event in the right atrium and a sensed event in the right ventricle. Sensed events are also referred to herein as depolarizations as they are representative of electrical depolarization of myocardial tissue. Paced events are also referred to herein as evoked responses. Paced events in the atria are triggered by A-pulses. Paced events in the ventricles are triggered by V-pulses. Finally, the term "intrinsic delay", as used herein, refers to the delay between a paced or sensed event in one chamber and a subsequent depolarization in another chamber. For example, an "intrinsic atrioventricular delay" refers to the delay between a paced or sensed atrial event and a subsequent sensed ventricular event, e.g. an AS-VS or AP-VS delay. An "intrinsic inter-atrial delay" refers to the delay between a paced or sensed event in one atrial chamber and a subsequent sensed event in the other atrial chamber, e.g. an $AS_R$-$AS_L$ or $AP_R$-$AS_L$.

For many patients, particularly those with congestive heart failure (CHF), it is desirable to identify a set of control parameters that will yield optimal cardiac performance (also referred to as hemodynamic performance). Cardiac performance is a measure of the overall effectiveness of the cardiac system of a patient and is typically represented in terms of stroke volume or cardiac output. Stroke volume is the amount of blood ejected from the left ventricle during systole in a forward direction. Cardiac output is the volume of blood pumped by the left ventricle per minute (or stroke volume times the heart rate). In view of the importance of maintaining optimal cardiac performance, especially for patients with compromised cardiac function, it would be desirable to provide improved techniques for use with pacemakers or ICDs for identifying pacing control parameters that optimize cardiac performance, particularly to reduce the degree of heart failure and valvular regurgitation. It is to this end that aspects of the invention are generally directed.

It is particularly desirable to identify A-VP delay values providing the best cardiac performance. In normal patients, the electrical conduction through the AV node is intact, and the body automatically adjusts the delay via the circulating hormones and the autonomic nervous system according to its physiologic state. It is well known, for example, that in normal patients the intrinsic AS-VS delay shortens with increasing heart rate associated with a physiologic stress such as exercise. For patients with abnormal AV node conduction or complete heart block, a pacemaker can control the A-VP pacing delay by delivering a ventricular pacing pulse at a software-controlled delay after an atrial pace or atrial sensed event. Since the optimum A-VP delay varies from person to person, this parameter should be optimized on an individual basis.

Conventionally, the physician attempts to program the A-VP delay (or other parameters) for a given patient by using an external programmer to control the device implanted within the patient to cycle through a set of different A-VP delay values. For each value, the implanted device paces the heart of the patient for at least a few minutes to permit hemodynamic equilibration, then the physician records a measure of the resulting cardiac performance, measured, for example, using Doppler echocardiography. The A-VP delay value that yields the best cardiac performance is then selected and programmed into the device. However, this is a time consuming and potentially expensive procedure. As a result, some physicians do not bother to optimize A-VP delay in many of their patients. Rather, A-VP delay is merely set to a default value and is adjusted only if the patient does not respond well to pacing therapy or complains that they do not feel well. Hence, many patients are not paced at their particular optimal A-VP delay value and thus do not obtain the maximal potential benefit from the improved cardiac performance that could be gained with the optimal A-VP delay. Moreover, even in circumstances wherein A-VP delay is optimized by the physician using, for example, Doppler echocardiography, the time and associated costs are significant. In addition, the optimal A-VP delay for a particular patient may change with time due to, for example, progression or regression in CHF, changes in medications, and/or changes in overall fitness. However, with conventional optimization techniques, the A-VP delay is re-optimized, if at all, only during specially scheduled follow-up sessions with the physician to allow access to the noninvasive testing equipment such as Doppler-echocardiography, which may be months or perhaps years apart.

Accordingly, it is would be highly desirable to provide improved techniques for more easily and reliably determining optimal or otherwise preferred A-VP delay values for a particular patient. At minimum, such techniques should be designed so as to be performed by an external programmer using only IEGM data received from the implanted device along with otherwise routine surface EKG data, so that Doppler echocardiography or other expensive and time consuming cardiac performance monitoring techniques are not required. Moreover, depending upon the implanted device and its leads, the improved techniques should be designed so as to be performed by the implanted device itself, without even surface EKG data. The latter technique would permit the optimal A-VP delay to be frequently and automatically updated so as to respond to changes within the patient. It is to these ends that aspects to the invention are more specifically directed.

Note that some techniques have been proposed for determining an optimal A-VP delay value based on IEGM data. For example, it has been proposed that the A-VP delay be set to A-VP=0.7 A-$VS_R$-55 ms. Although this allows the A-VP pacing delay to be set automatically by the implanted device, it is not believed that the formula reliably provides the optimal delay value for many patients. In particular, the formula only takes into account the intrinsic delay from the atria to the right ventricle (A-$VS_R$) but does not take into account the intrinsic inter-atrial delay or the intrinsic delay from the atria to the left ventricle, which the present inventors believe can significantly affect the optimal A-VP delay in at least some patients. In addition, it is desirable to separately determine optimal delay values for paced and sensed events, i.e. separate values for AS-VP and for AP-VP. Accordingly, still other aspects of the invention are directed to providing improved optimization techniques that take into account intrinsic inter-atrial delay, intrinsic delay times to both the left and right ventricles, and which provide separate optimal delay values based on paced and sensed atrial events.

SUMMARY OF THE INVENTION

In accordance with the invention, techniques are provided for determining preferred or optimal atrioventricular (A-VP) delay values for use in delivering cardiac pacing therapy to the heart of a patient in which an implantable cardiac stimulation device is implanted. Briefly, both an intrinsic inter-atrial conduction delay and an intrinsic atrioventricular conduction delay are determined for the patient. Then, the preferred A-VP delay for use with the patient is determined based on the intrinsic inter-atrial delay in combination with the intrinsic atrioventricular delay. By taking into account intrinsic inter-atrial delay along with intrinsic atrioventricular delay, it is believed that a more reliable estimate of the true optimal A-VP delay values for the patient can be achieved than with techniques that only take into account intrinsic atrioventricular delay values. Moreover, the intrinsic inter-atrial delay can be determined based on a combination of IEGM signals and surface EKG signals or, if the device is equipped with the appropriate leads for separately sensing left and right atrial IEGM signals, then the intrinsic inter-atrial delay can be determined based solely on IEGM signals. Hence, the preferred A-VP delay can readily be determined either by an external programmer based on IEGM signals and surface EKG signals or, if the so equipped, by the implanted device itself based only on IEGM signals. In either case, cardiac performance monitoring techniques such as Doppler echocardiography are not required.

In one example, wherein the implanted device is not equipped to sense both left and right atrial IEGM signals, intrinsic inter-atrial delay values are determined based on a comparison of atrial IEGM signals derived from the right atrium and a corresponding surface EKG signals. More specifically, separate intrinsic inter-atrial delay values are determined for atrial sensed events and atrial paced events. For sensed atrial events, the intrinsic inter-atrial delay ($AS_R$-$AS_L$) is determined by taking the width of a sensed atrial depolarization ("$AS_{WIDTH}$") as it appears within the A-IEGM signal and adding an correction value ("$AS_{CORRECTION}$") that is equal to the time difference between the end of the atrial depolarization of the A-IEGM signal and the end of the corresponding P-wave of the surface EKG. For paced atrial events, the intrinsic inter-atrial delay ($AP_R$-$AS_L$) for a base pacing rate is determined by taking the width of an atrial evoked response ("$AP_{WIDTH}$") as it appears within the A-IEGM signal and adding a correction value that is equal to the time difference between the end of the evoked response of the A-IEGM signal and the end of the corresponding P-wave of the surface EKG. Preferably, both the paced and sensed intrinsic inter-atrial delay values are averaged over some suitable number of events, preferably at least 10-20 within a predefined rate range.

Meanwhile, intrinsic atrioventricular delay values are determined based on a comparison of A-IEGM signals and left and right ventricular IEGM signals ("$V_L$-IEGM" and "$V_R$-IEGM", respectively), again for both paced and sensed atrial events. For a sensed event, an intrinsic atrioventricular delay value for the left ventricle (AS-$VS_L$) is determined based on the time delay between the peak of a sensed atrial depolarization in the A-IEGM signal and the peak of the corresponding sensed QRS complex in the $V_L$-IEGM signal, or between other consistent reference points. Typically, the A-IEGM signal is sensed in the right atrium and so the calculated atrioventricular delay value represents $AS_R$-$VS_L$, though the delay value may instead be derived from an A-IEGM signal sensed in the left atrium or may be based on a combined left and right A-IEGM signal. Likewise, an intrinsic atrioventricular delay value for the right ventricle (AS-$VS_R$) is determined based on the time delay between the peak of the atrial depolarization and the peak of the corresponding QRS complex in the $V_R$-IEGM signal, or between other consistent reference points. The smaller of the AS-$VS_L$ and AS-$VS_R$ delay values is then selected to represent AS-VS for the purposes of calculating a preferred value for AS-VP. Similar procedures are followed to derive a single value for AP-VS for use in calculating a preferred value for AP-VP using the peak of an evoked response in the A-IEGM signal and the peaks of QRS complexes in the left and right V-IEGM signals, or other consistent reference points. Preferably, the derived values for AS-VP and AP-VP are separately averaged over some minimum number of events, again typically at least 10-20 within a predefined rate range. Multiple assessments may be made of sensed and paced atrial events with respect to ventricular conduction at various rate ranges.

Finally, preferred AS-VP and AP-VP delay values are separately calculated. To calculate a preferred value for AS-VP, an offset value is specified based on the width of the atrial depolarization of the A-IEGM signal (i.e. based on $AS_{WIDTH}$.) If the width exceeds a threshold value of 100 milliseconds (ms), the offset is set to 30 ms. Otherwise, the offset is set to 60 ms. Other appropriate threshold and offset values may be used. Then, a pair of candidate AS-VP delay values ($AS$-$VP_1$ and $AS$-$VP_2$) is determined as follows:

$$AS\text{-}VP_1 = \alpha*((AS\text{-}VS)-(AS\text{-}AS))+AS_{WIDTH}$$

$$AS\text{-}VP_2 = AS\text{-}AS + \text{offset}$$

where $\alpha$ is a predetermined coefficient set to, for example, 0.5. The smaller of the two candidate values is then selected as the preferred AS-VP delay value for use with ventricular pacing. Alternatively, either just $AS\text{-}VP_1$ or $AS\text{-}VP_2$ is calculated or selected. The preferred AS-VP delay value may thereafter be adjusted based on intrinsic heart rate.

To calculate a preferred value for AP-VP, a different threshold is used for specifying the offset. If the width of the evoked response in the atria exceeds a threshold value of 120 ms, the offset is set to 30 ms. Otherwise, the offset is set to 60 ms. Again, other appropriate threshold and offset values may be used. Then, a pair of candidate AP-VP delay values ($AP\text{-}VP_1$ and $AP\text{-}VP_2$) is determined as follows:

$$AP\text{-}VP_1 = \alpha*((AP\text{-}VS)-(AP\text{-}AS))+AP_{WIDTH}$$

$$AP\text{-}VP_2 = AP\text{-}AS + \text{offset}$$

where $\alpha$ is the same predetermined coefficient.

The smaller of the two candidate values is then selected as the preferred AP-VP delay value for use with ventricular pacing. Again, alternatively, either just $AP\text{-}VP_1$ or $AP\text{-}VP_2$ is calculated or selected. The preferred AP-VP delay value may thereafter be adjusted based on current pacing rate.

It is believed that the preferred AS-VP and AP-VP delay values calculated in this manner represent optimal delay values in that the values tend to maximize ventricular filling so as to maximize cardiac performance. However, even if the delay values differ from true optimal values, they nevertheless represent preferred delay values likely to improve ventricular filling. Preferably, both delay values (AS-VP and AP-VP) are calculated and used. Alternatively, a preferred AS-VP value could be calculated and used in conjunction with an AP-VP value selected using otherwise conventional techniques, or vice versa.

Thus, for implantable devices not equipped to sense both left and right atrial IEGM signals, preferred A-VP delay values are determined based on a comparison of IEGM signals and surface EKG signals. The determination is preferably performed by an external programmer, with the preferred delay values then reviewed by a physician then downloaded to the implanted device for use therein.

For implantable devices equipped to sense both left and right atrial IEGM signals, the determination of preferred A-VP delay values is instead made based only IEGM signals without need for surface EKG signals. As with the foregoing technique, separate intrinsic inter-atrial delay values are determined for atrial sensed events and atrial paced events. For sensed atrial events, an intrinsic $AS_R\text{-}AS_L$ delay is determined by measuring the time delay between the end of an atrial depolarization as it appears within a right atrial IEGM signal and the end of the same atrial depolarization as it appears within a left atrial IEGM signal derived, for example, from a coronary sinus (CS) lead having a left atrial electrode. For paced atrial events, the intrinsic inter-atrial delay is determined by measuring the time delay between the end of an evoked response as it appears within the right atrial IEGM signal and the end of the same evoked response as it appears within the left atrial IEGM signal. Intrinsic atrioventricular delay values (i.e. AS-VS and AP-VS delay values) are determined using the same techniques as summarized above. Preferred AS-VP and AP-VP delay values are derived, again using the same techniques as summarized above. Since the determination of the preferred AS-VP and AP-VP delay values is made without requiring a surface EKG, the determination is preferably performed by the implanted device itself rather than the external programmer. The determination is repeated as often as needed to update the AS-VP and AP-VP delay values to respond to possible changes within the patient.

Thus, improved techniques are provided for more easily and reliably determining preferred A-VP delay values for a particular patient. As noted, one exemplary technique is performed by an external programmer using only IEGM data received from the implanted device along with otherwise routine surface EKG data, and so Doppler echocardiography or other expensive and time consuming cardiac performance monitoring techniques are not required. The other exemplary technique is performed by the implanted device itself, without requiring surface EKG data, thus permitting the preferred A-VP delay values to be frequently and automatically updated. Moreover, both techniques take into account the intrinsic inter-atrial delay of the patient as well as intrinsic $A\text{-}VS_L$ and $A\text{-}VS_R$ delay values, providing for a more reliable estimate of the optimal A-VP delay values than techniques that utilize only right-sided measurements ($A\text{-}VS_R$ values). Moreover, as noted, separate values are determined for AS-VP and AP-VP delays to provide for further optimization. Other features, objects and advantages are provided as well. System and method implementations are set forth.

BRIEF DESCRIPTION OF THE DRAWINGS

The above and further features, advantages and benefits of the invention will be apparent upon consideration of the present description taken in conjunction with the accompanying drawings, in which.

DETAILED DESCRIPTION OF THE PREFERRED EMBODIMENTS

The following description includes the best mode presently contemplated for practicing the invention. This description is not to be taken in a limiting sense but is made merely to describe general principles of the invention. The scope of the invention should be ascertained with reference to the issued claims. In the description of the invention that follows, like numerals or reference designators will be used to refer to like parts or elements throughout.

Figure 1:
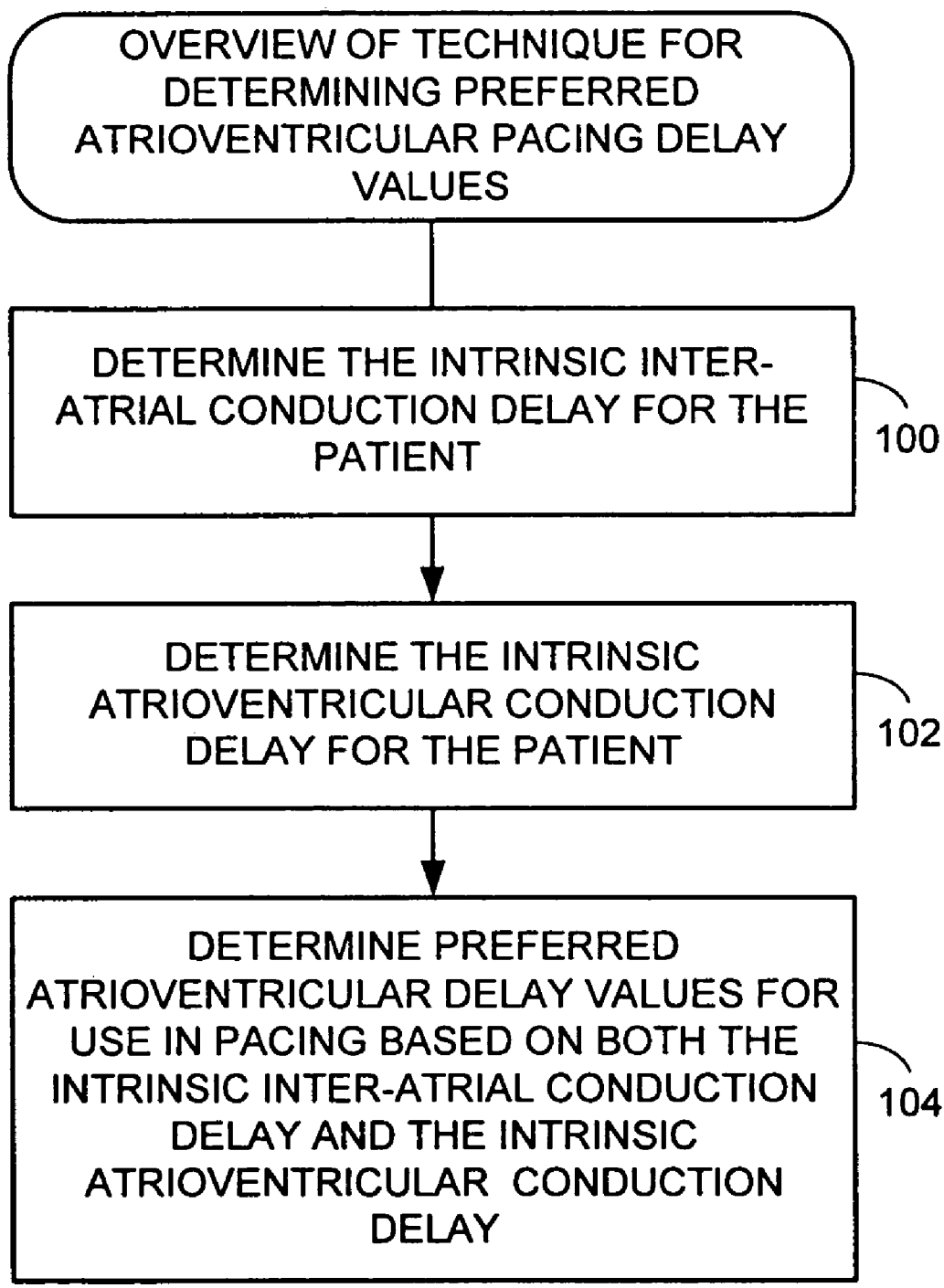
FIG. 1 is a flow chart providing an overview of techniques provided in accordance with the invention for identifying preferred A-VP delay values based on both intrinsic inter-atrial delay values and intrinsic atrioventricular delay values.

Briefly, an overview of the A-VP delay optimization techniques of invention will first be provided with reference to FIG. 1. Then, exemplary techniques for use within an implantable system not equipped to sense both left and right atrial IEGM signals will described with reference to FIGS. 2-7. Next, an exemplary embodiment for use with an implanted device equipped to sense both left and right atrial IEGM signals will be described with reference to FIGS. 8 and 9. Finally, details of an exemplary implanted device and an exemplary external programmer will be provided with reference to FIGS. 10-12.

Overview of Techniques for Determining Preferred A-VP Delay

Within FIG. 1, at step 100, the intrinsic inter-atrial conduction delay for the patient is determined. The intrinsic inter-atrial conduction delay represents the propagation time delay for electrical signals conducted from one atrium to the other via myocardial tissue. In other words, it is time in which "near field" signals are conducted via myocardial tissue from one atrium to the other. If the device is equipped to sense both left and right atrial IEGM signals, this determination may be made by sensing a single atrial electrical event (either a native atrial depolarization or an evoked response within the atria) within both the left and right atria and then measuring the time difference there-between. Otherwise, this determination is instead made based upon examination of the width of an atrial event (again either a native atrial depolarization or an atrial evoked response) in combination with a P-wave sensed using a surface EKG. Here, the term P-wave refers to the feature of the surface EKG that corresponds to an atrial depolarization or atrial evoked response appearing in the A-IEGM signal. Typically, the P-wave differs in shape and width from the corresponding feature of the A-IEGM. Next, at step 102, the intrinsic atrioventricular conduction delay is determined for the patient. The intrinsic atrioventricular delay represents the time delay for electrical signals to be conducted from the atria to the ventricles via myocardial tissue, i.e. it is time in which "near field" signals are conducted via myocardial tissue from the atria to the ventricles. This determination may be made by detecting atrial electrical events and subsequent intrinsic ventricular depolarization events using implanted leads. As will be explained below, separate intrinsic atrioventricular delay values may be determined for the left and right ventricles. Once both the intrinsic inter-atrial delay and atrioventricular delay values have been determined then, at step 104, preferred or optimal A-VP pacing delay values are determined based upon the intrinsic delay values.

By taking into account the intrinsic inter-atrial delay as well as the intrinsic atrioventricular delay, preferred or optimal A-VP delay values can be reliably determined without requiring complicated conventional techniques such as the use of Doppler echocardiography and the like. Depending upon whether the device is equipped to sense both left and right atrial IEGM signals, the steps of FIG. 1 may be performed by the implanted device (FIGS. 10-11) itself or may be performed in part by the implanted device and in part by an external programmer (FIG. 12). For implementations in which the entire determination is performed by the implanted device, the preferred or optimal A-VP delay values can thereby be recalculated as often as needed, based upon newly sensed atrial and ventricular IEGM signals, to update the A-VP delay values to maintain them at optimal values. Even in implementations where an external programmer is employed (i.e. implementations that utilize a surface EKG to aid in the determination of the intrinsic inter-atrial delay), substantial benefits are still gained as compared to conventional A-VP delay optimization techniques requiring Doppler echocardiography or the like. In particular, during routine follow-up sessions between patient and physician, the optimal or preferred A-VP delay can be easily recalculated and reprogrammed based only upon electrical cardiac signals sensed by the implanted device in combination with a surface EKG. By eliminating the need for Doppler echocardiography the like, costs are reduced and the physician is more likely to properly optimize the A-VP delay rather than merely set them to default or other arbitrary values. Hence, the patient benefits from improved cardiac performance.

Optimization Technique for use with Surface EKG

Figure 2:
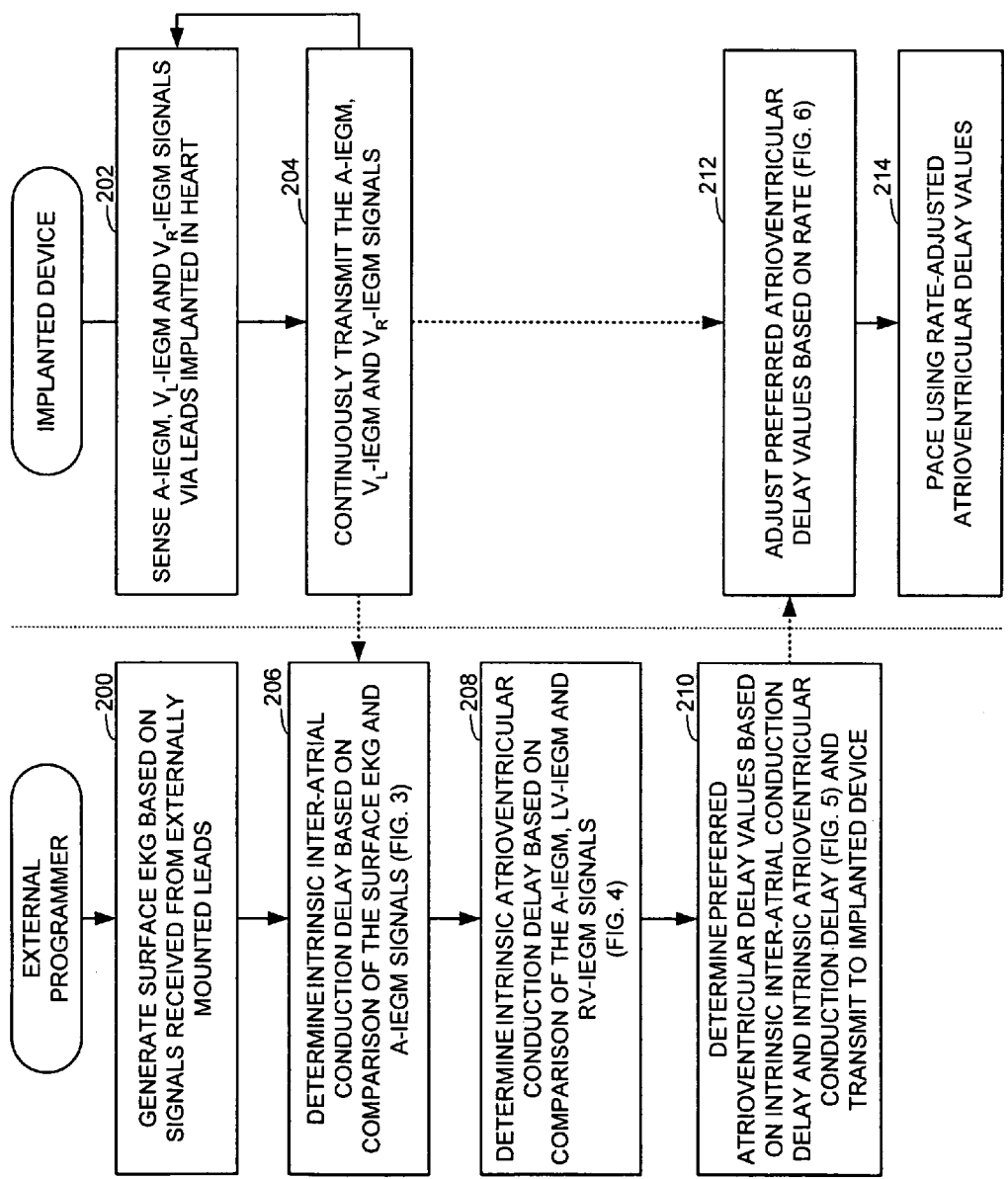
FIG. 2 is a flow chart illustrating an exemplary technique for identifying preferred A-VP delay values in accordance with the general techniques of FIG. 1 for use with an implantable device not equipped to sense both left and right atrial IEGM signals.

Referring now to FIG. 2, an exemplary technique for use with an implanted system that is not equipped to sense both left and right atrial IEGM signals will now be described. The intrinsic inter-atrial delay is therefore estimated based on comparison of electrical cardiac signals sensed by the device in combination with surface EKG signals. Hence, the determination of the preferred or optimal A-VP delay is performed, in this implementation, by software operating within the external programmer. Within FIG. 2, steps performed by the external programmer are shown the left; steps performed by the implanted device are shown on the right. Beginning at step 200, the external programmer generates a surface EKG based upon signals received from the leads externally mounted on the chest of the patient. (In FIG. 2, the surface EKG leads are not separately shown.) Simultaneously, at step 202, the implanted device senses electrical cardiac signals via leads implanted in the heart of the patient. More specifically, the implanted device senses at least one atrial channel IEGM signal (A-IEGM) and separate left and right ventricular channel IEGM signals ($V_L$-IEGM and $V_R$-IEGM) using otherwise conventional sensing techniques. At step 204, the implanted device transmits the A-IEGM, $V_L$-IEGM and $V_R$-IEGM signals to the external programmer using conventional telemetry techniques. Other data may be transmitted as well, such as event marker data identifying events detected within the IEGM signals. Steps 202 and 204 are performed in a loop to continuously or periodically transmit the data from implanted device to the external programmer, which receives and processes data along with the contemporaneous surface EKG signals.

At step 206, the external programmer determines the intrinsic inter-atrial conduction delay based on comparison of the surface EKG and the A-IEGM signals. This is described in more detail below with reference to FIG. 3. At step 208, the external programmer then determines the intrinsic atrioventricular conduction delay based upon a comparison of A-IEGM, $V_L$-IEGM and $V_R$-IEGM signals received from the implanted device. This is described in greater detail below with reference to FIG. 4. Note that, depending upon the particular types of data transmitted by the implanted device, the external programmer may receive data specifying the intrinsic atrioventricular conduction delay directly from the implanted device so that the external programmer need not perform this calculation itself. In any case, at step 210, the external programmer then determines the separate preferred AS-VP and AP-VP delay values based on a comparison of the intrinsic inter-atrial delay and the intrinsic atrioventricular delay and transmits these values to the implanted device. This determination will be described below in greater detail with reference to FIG. 5. The preferred AS-VP and AP-VP delay values are received by the implanted device at step 212, which stores the values therein. Before applying the preferred delay values during pacing, the implanted device adjusts the values the based upon current intrinsic heart rate or current pacing rate so as to optimize the delay values for the particular rate. Adjustment of the delay values based on rate is described with reference to FIG. 6. Finally, at step 214, the implanted device paces the heart of the patient in accordance with otherwise conventional pacing techniques using the rate-adjusted AS-VP and AP-VP delay values. In this manner, improved cardiac performance may be obtained.

The steps performed by the external programmer of FIG. 2 are performed under the control of a physician or other medical professional who can review the preferred AS-VP and AP-VP delay values determined by the external programmer, verify that they are within acceptable bounds, and adjust if desired. In addition, the physician may use otherwise conventional techniques to verify that the preferred AS-VP and AP-VP delay values provide for an improved stroke volume. It is anticipated that the steps of FIG. 2 will be performed by physicians during an initial programming session and during subsequent follow-up sessions with the patient. Hence, if the optimal AS-VP and AP-VP values for the particular patient change, perhaps as a result of progression or regression of heart disease or the administration of medications, the optimal delay values calculated by the external programmer can be periodically updated by repeating the steps of FIG. 2.

Figure 3:
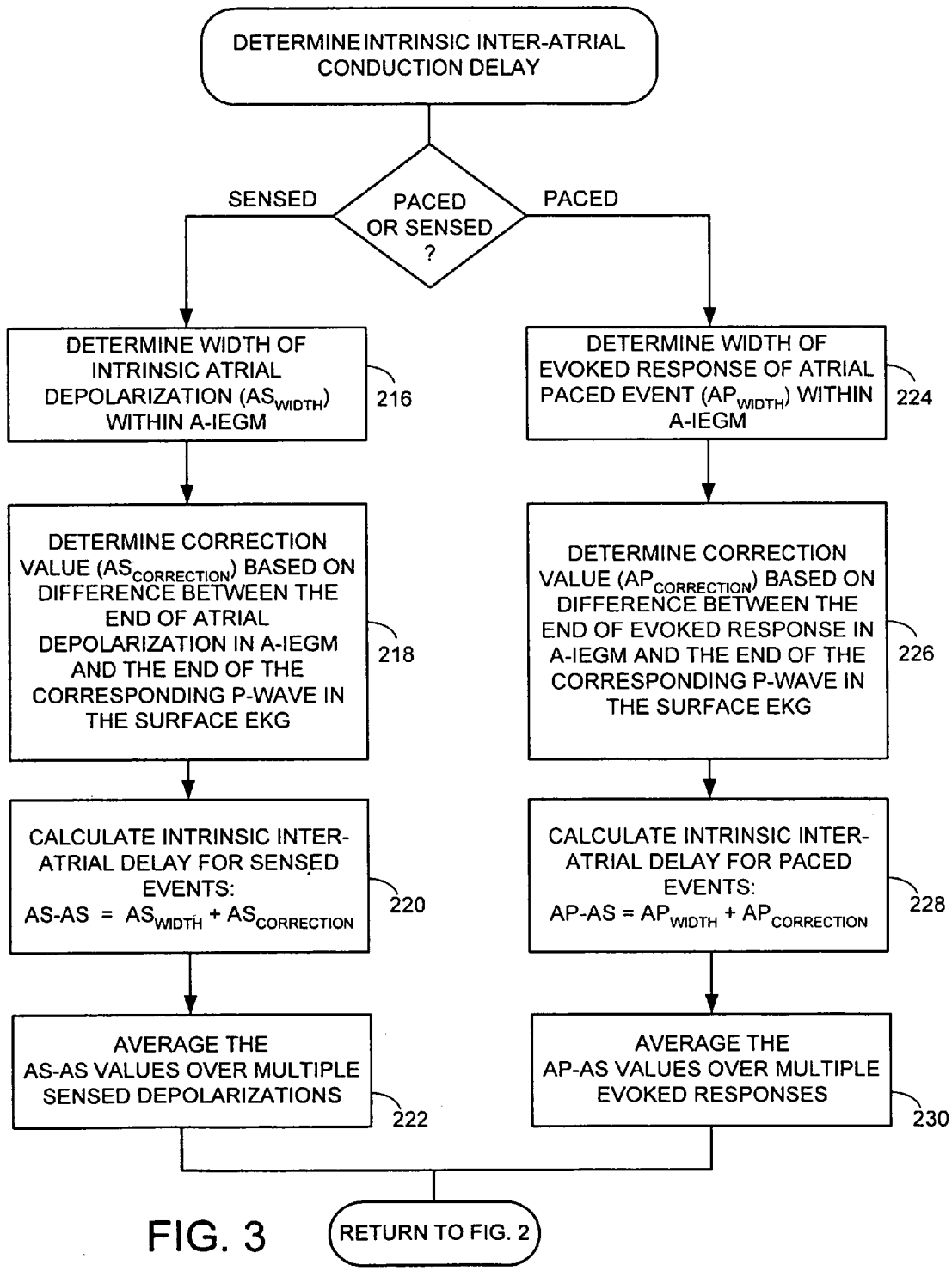
FIG. 3 is a flow chart illustrating an exemplary technique for determining intrinsic inter-atrial delay values based on atrial IEGM signals and surface EKG signals for use with the technique of FIG. 2.

FIG. 3 provides an example of a technique for determining the intrinsic inter-atrial delay for use at step 206 of FIG. 2. The specific technique depends upon whether the atrial events are paced or sensed. Processing of sensed events is shown on the left side of FIG. 3; processing of paced events is shown on the right side. Considering sensed events first, at step 216, the external programmer first determines the width of a sensed intrinsic atrial depolarization within the A-IEGM signal (i.e. $AS_{WIDTH}$). This width may be determined within the A-IEGM signal by identifying the beginning and end of the atrial depolarization. Otherwise conventional detection techniques may be employed to detect the beginning of the event. An improved technique for detecting the end of the events is described below with reference to FIG. 7. Note also that, if the implanted device is configured to provide a value indicative of the width of an atrial depolarization, then the external programmer need not repeat this determination at step 216 and may instead simply use the value provided by the implanted device.

Next, at step 218, the external programmer determines the difference, if any, between the end of the atrial depolarization within the A-IEGM signal and the end of the corresponding P-wave in the surface EKG signal. This difference is referred to herein as $AS_{CORRECTION}$. The value detected for the end of the atrial depolarization for use at step 216 may be also used at step 218. Otherwise conventional techniques may be employed for determining the end of the P-wave within the surface EKG. In any case, the external programmer subtracts one time value from the other to determine the correction value. Note that, with suitable choice of EKG lead, the end of the P-wave within the surface EKG should always occur after the end of a corresponding atrial depolarization sensed within the A-IEGM signal and hence the correction value will be a positive value. If a negative correction value is nevertheless detected, it is preferably discarded as being erroneous or as being the result of anomalous conditions.

At step 220, the external programmer then calculates a value for the intrinsic inter-atrial delay for sensed atrial events (i.e. $AS_R$-$AS_L$) by adding $AS_{WIDTH}$ and $AS_{CORRECTION}$ as follows:

$$AS\text{-}AS=AS_{WIDTH}+AS_{CORRECTION}.$$

This provides one value for the intrinsic inter-atrial delay based on one sensed atrial depolarization. Preferably, the external programmer averages intrinsic inter-atrial delay values over multiple atrial depolarizations, preferably at least 10 or 20.

For paced events, the external programmer performs a similar sequence of steps using the evoked response triggered by an A-pulse. Beginning at step 224, the external programmer determines the width of the evoked response within the A-IEGM channel signal received from the implanted device. The width of the evoked response is referred to herein as $AP_{WIDTH}$. The width is determined by identifying the beginning and the end of an individual evoked response. The techniques described below for FIG. 7 and may be employed to identify the end of the evoked response. Conventional techniques may be used to detect the beginning of the event. In addition, as with sensed events, if the implanted device itself provides a value for $AP_{WIDTH}$ then the external programmer need not repeat this determination and can instead use the value provided by the implanted device. At step 226, the external programmer then compares the surface EKG and the A-IEGM signal and determines the difference between the end of the evoked response within the A-IEGM signal and the end of the corresponding P-wave in the surface EKG signal. This difference is referred to herein as $AP_{CORRECTION}$. At step 228, the $AP_{WIDTH}$ and the $AP_{CORRECTION}$ values are then added to yield a value for the intrinsic inter-atrial delay for the paced event using the following equation:

$$AP\text{-}AS=AP_{WIDTH}+AP_{CORRECTION}.$$

This provides one intrinsic AP-AS value based on one atrial evoked response. Preferably, at step 230, the external programmer averages multiple AP-AS values over multiple evoked responses, preferably at least 10 or 20.

Hence, upon completion of the steps of FIG. 3, the external programmer has calculated an averaged AS-AS value and an average AP-AS value. (Note that it may be necessary for the external programmer to control the implanted device to selectively pace the atria and selectively allow the atria to beat intrinsically, so as to insure that the A-IEGM signal includes both evoked responses as well as intrinsic atrial depolarizations.)

Also, note that techniques have been developed for emulating a surface EKG using internal electrical cardiac signals. See, for example, U.S. patent application Ser. No. 10/735,948 of Kil et al., filed Dec. 12, 2003, entitled "System and Method for Emulating a Surface EKG Using Internal Cardiac Signals Sensed by an Implantable Medical Device" which is incorporated by reference herein. See also, U.S. patent application Ser. No. 10/334,741 to Kroll et al., entitled "System and Method for Emulating a Surface EKG Using Implantable Cardiac Stimulation Device", filed Dec. 30, 2002, which is also incorporated by reference herein. If the implanted device is capable of reliably emulating a surface EKG, then steps 218 and 226 may be performed using the emulated surface EKG signals rather than actual surface EKG signals. If so, a surface EKG need not be employed, allowing the external programmer to determine the intrinsic inter-atrial conduction delay based entirely upon signals sensed by the implanted device, i.e. the external programmer uses the P-wave from the emulated surface EKG to correct the width of the atrial events within the A-IEGM. Alternatively, the implanted device itself may utilize the emulated surface EKG to make the determination, thus allowing the device to automatically and directly optimize the A-VP delay without the use of an external programmer. In such an implementation, it is nevertheless desirable for the physician to periodically review the optimal AS-VP and AP-VP delay values identified by the implanted device to verify that they are within acceptable ranges. Additionally, predetermined acceptable ranges may be programmed into the implantable device such that, should be device identify delay values outside the ranges, the device can be programmed to then instead utilize default delay values, pending review by a physician during a subsequent follow-up session.

Figure 4:
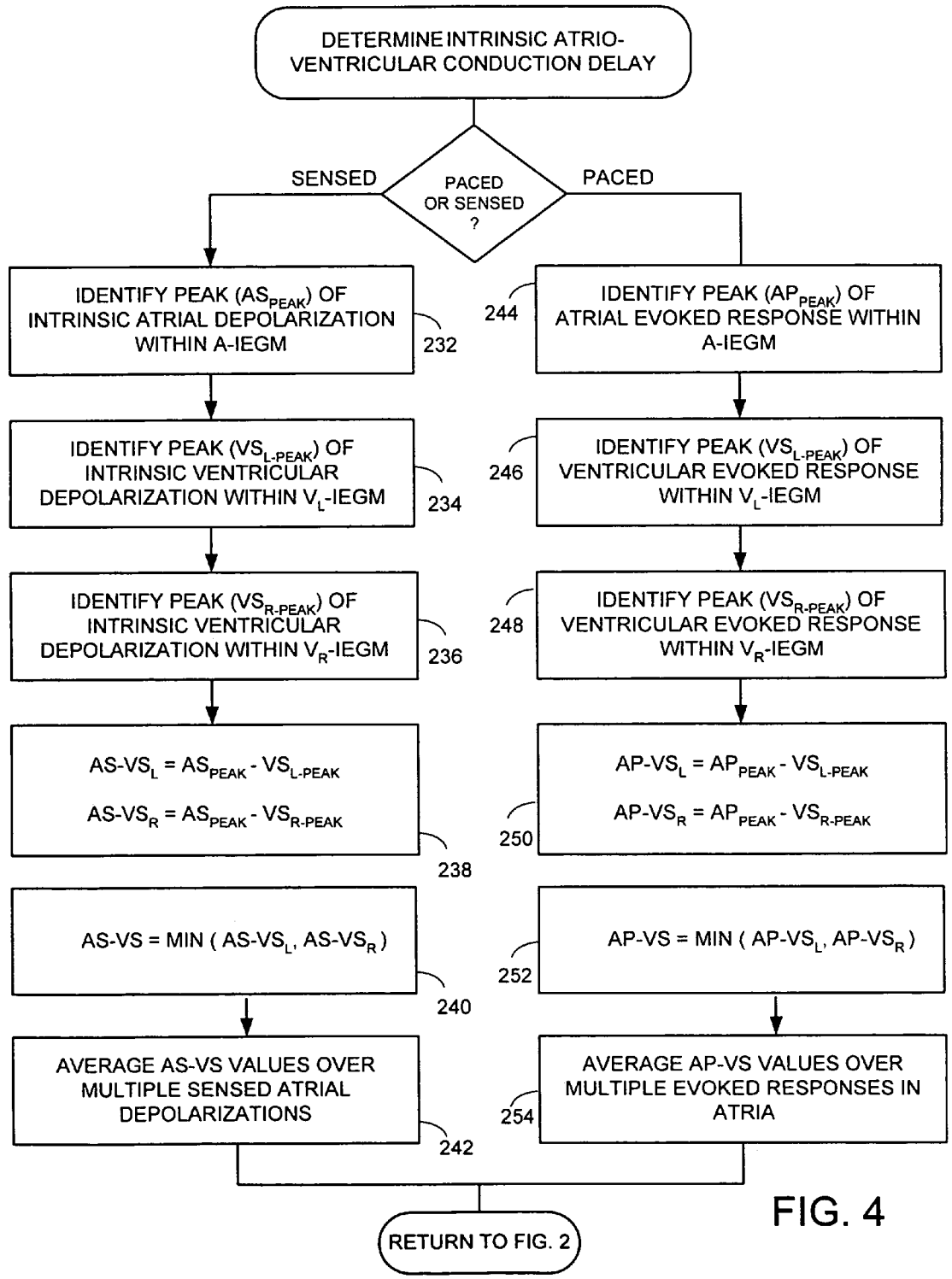
FIG. 4 is a flow chart illustrating an exemplary technique for determining intrinsic atrioventricular delay values for use with the technique of FIG. 2.

Referring now to FIG. 4, an exemplary technique for determining the intrinsic atrioventricular delay for use at step 208 of FIG. 2 will now be described. As with the technique of FIG. 3, the specific steps of FIG. 4 depend upon whether atrial events are sensed or paced. For sensed events, at step 232, the external programmer identifies the peak of the intrinsic atrial depolarization by examining the A-IEGM signal. The peak is referred to herein as $AS_{PEAK}$. Otherwise conventional techniques may be employed for identifying the peak of the atrial depolarization. If the implanted device itself is capable of identifying the peak and transmits that data to the external programmer, then the external programmer need not repeat this determination and may instead use value provided by the implanted device. At step 234, the external programmer identifies the peak of the subsequent intrinsic ventricular depolarization within the left ventricular IEGM signal ("$VS_{L-PEAK}$".) At step 236, the peak of intrinsic ventricular depolarization within the right ventricular IEGM signal channel is also identified ($VS_{R-PEAK}$".) Again, if the implanted device is capable of providing this information, the external programmer need not repeat the determination. In any case, at step 238, the programmer then calculates intrinsic atrioventricular delay values for both the left and right ventricles based on $AS_{PEAK}$, $VS_{L-PEAK}$, and $VS_{R-PEAK}$:

$$AS\text{-}VS_L = AS_{PEAK} - VS_{L-PEAK}$$

$$AS\text{-}VS_R = AS_{PEAK} - VS_{R-PEAK}.$$

At step 240, the programmer then selects the smaller of the two intrinsic AS-VP delay values, which is thereafter used as the AS-VS value for the purposes of calculating the optimal AS-VP. Alternatively, either $AS\text{-}VL_L$ or $AS\text{-}VL_R$ is selected as the AS-VS value.

$$AS\text{-}VS = \text{MIN}(AS\text{-}VS_L, AS\text{-}VS_R)$$

Note that the use of the peaks of the atrial and ventricular depolarizations is merely an example. Other consistent reference points may instead be used, such as the beginning or end of a depolarization.

If the implanted device does not include sensing leads in both left and right ventricles, then only a single VS peak value is identified and the AS-VS value is calculated based on the single peak VS value in combination with the peak of the atrial depolarization. In any case, steps 232-240 provide for calculation of a single AS-VS value. Preferably, at step 242, AS-VS values are averaged over multiple intrinsic heartbeats, preferably at least 10 or 20.

A similar sequence of steps performed in connection with paced atrial beats. Briefly, beginning at step 244, the external programmer identifies the peak of an evoked response within the A-IEGM signal ($AP_{PEAK}$). At step 246 and 248, peaks within the corresponding ventricular depolarization, as sensed with the left and right ventricles are identified. Steps 250 and 252 are performed to calculate a single intrinsic AP-VS value using the following equations:

$$AP\text{-}VS_L = AP_{PEAK} - VS_{L-PEAK}$$

$$AP\text{-}VS_R = AP_{PEAK} - VS_{R-PEAK}$$

$$AP\text{-}VS = \text{MIN}(AP\text{-}VS_L, AP\text{-}VS_R).$$

As noted above, the use of peaks within the atrial and ventricular signals is merely exemplary. Other consistent reference points may instead be used.

At step 254, AP-VS values for multiple evoked responses are averaged together to yield an averaged AP-VS value for subsequent use. As with the determination of the intrinsic inter-atrial delay, it may be necessary for the external programmer to control the device to selectively pace the atria and to selectively allow the atrial to beat intrinsically so as to generate data for both paced and sensed atrial events. Note also that the calculations performed within FIG. 4 use only IEGM signals and do not require surface EKG signals. Accordingly, the steps of FIG. 4 may be performed by the implanted device itself, with the resulting average intrinsic AP-VS delay values then transmitted to the external programmer for storage and processing therein.

Figure 5:
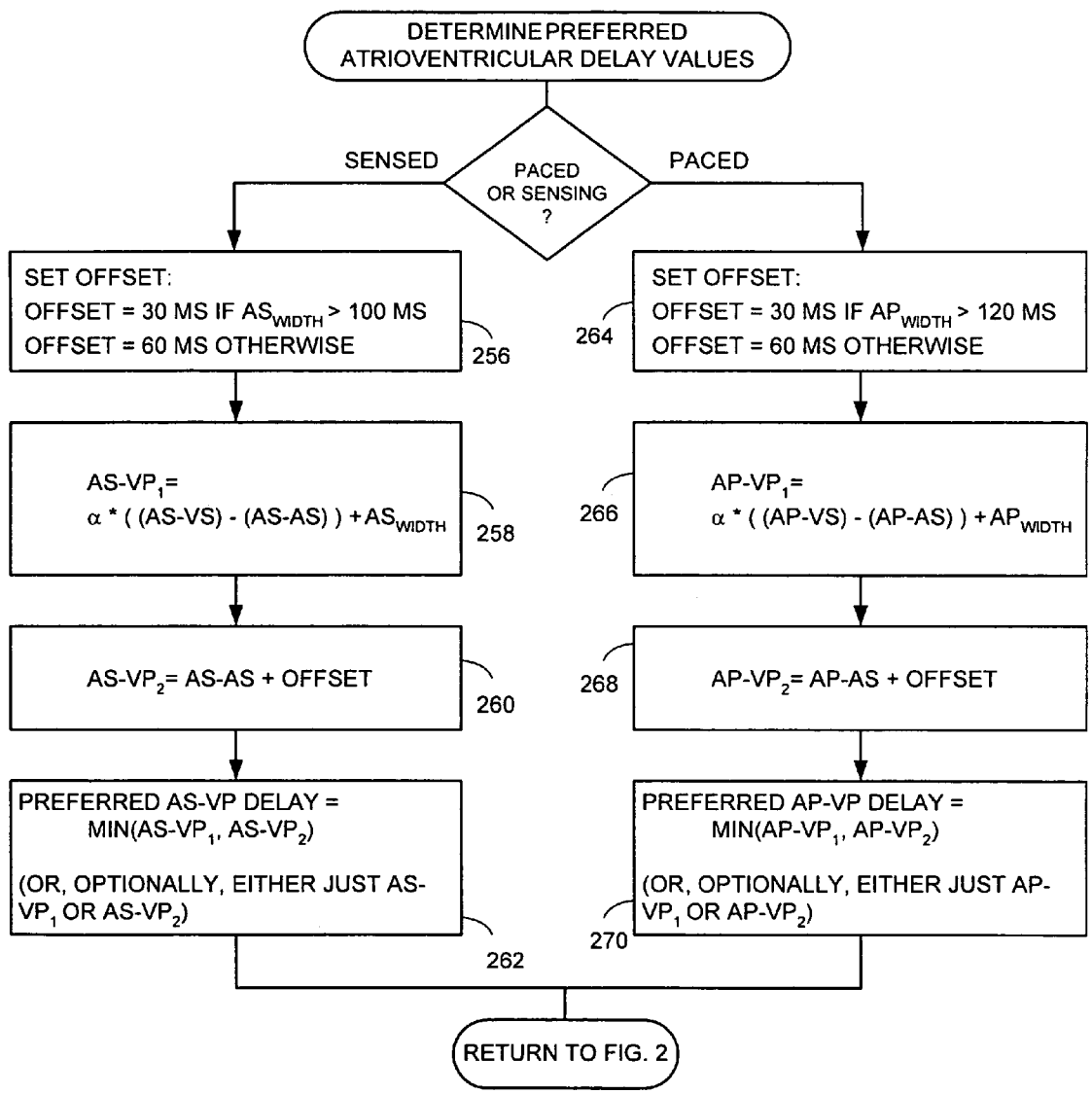
FIG. 5 is a flow chart illustrating an exemplary technique for determining optimal A-VP delay values based on the intrinsic inter-atrial and intrinsic atrioventricular delay values for use with the technique of FIG. 2.

Referring to FIG. 5, an exemplary technique for use at step 210 of FIG. 2 will now be described for use in determining optimal AS-VP and AP-VP delay values based upon data generated by the techniques of FIGS. 3 and 4. To calculate an optimal AS-VP, beginning at step 256, the external programmer first specifies an offset value based upon the average width of intrinsic atrial events sensed within the A-IEGM signal, i.e. based upon $AS_{WIDTH}$. If $AS_{WIDTH}$ is greater than a predetermined width-based threshold $W_1$ (e.g. 120 ms), then the offset value is set to $T_1$ (e.g. 30 ms.) If $AS_{WIDTH}$ is less than or equal to $W_1$, then the offset is instead set to $T_2$ (e.g. 60 ms.) The following equations summarize this determination:

Offset=30 ms if $AS_{WIDTH}$>120 ms

Offset=60 ms otherwise.

The values for $W_1$, $T_1$ and $T_2$ are merely exemplary values. Routine experimentation may be performed to identify optimal values for these parameters for use with the techniques invention. Then, at step 258, the programmer calculates a first candidate AS-VP delay value based upon the intrinsic atrioventricular delay and intrinsic inter-atrial delay values already calculated for sensed events as follows:

$$AS\text{-}VP_1 = \alpha^*((AS\text{-}VS)-(AS\text{-}AS))+AS_{WIDTH}.$$

In the foregoing, the coefficient α is a programmable value set to, for example, 0.5. Routine experimentation may be performed to identify optimal values for α for use with the techniques invention. At step 260, the external programmer calculates a second candidate AS-VP delay value, this time based upon only the intrinsic inter-atrial delay value and the aforementioned offset (i.e. the atrioventricular delay value is not used):

$$AS\text{-}VP_2 = AS\text{-}AS + \text{Offset}.$$

At step 262, the preferred or optimal AS-VP delay is then determined by selecting the smaller of the two candidate values as follows:

$$AS\text{-}VP = \text{MIN}(AS\text{-}VP_1, AS\text{-}VP_2).$$

It is believed that this value represents the optimal AS-VP delay for achieving optimal cardiac performance. At the very least, it represents a preferred AS-VP delay. Alternatively, if desired, the external programmer may be programmed to simply select either the first candidate value or the second candidate value, or to average the values together. The various values may be presented to the physician who is then prompted to select one of the candidate values.

Thus, steps 256-262 operate to determine a preferred or optimal AS-VP delay value. This value is transmitted to the implanted device, which uses value to time the delivery of ventricular pacing pulses following intrinsic atrial events in accordance with otherwise conventional techniques.

Similar steps are performed to identify an optimal or preferred AP-VP delay value. Briefly, at step 264, the external programmer again defines an offset value, this time based upon the average width of an evoked response and using a different threshold value. If $AP_{WIDTH}$ is greater than a predetermined width-based threshold $W_2$ (e.g. 100 ms), then the offset value is set to $T_1$ (e.g. 30 ms.) If $AP_{WIDTH}$ is less than or equal to $W_2$, then the offset is instead set to $T_2$ (e.g. 60 ms.) The following equations summarize this determination:

$$\text{Offset}=30 \text{ ms if } AP_{WIDTH} > 100 \text{ ms}$$

$$\text{Offset}=60 \text{ ms otherwise}.$$

The values for $W_2$, $T_1$ and $T_2$ are merely exemplary values. Routine experimentation may be performed to identify optimal values for these parameters for use with the techniques invention. Then, at steps 266 and 268, a pair of candidate AP-VP delay values is derived using the following equations (which exploit the AP-AS and AP-VS values calculated using techniques of FIGS. 3 and 4):

$$AP\text{-}VP_1 = \alpha^*((AP\text{-}VS)-(AP\text{-}AS))+AP_{WIDTH}$$

$$AP\text{-}VP_2 = AP\text{-}AS + \text{Offset}.$$

The coefficient α may be same as used above for AS-VP, i.e. 0.5, or may differ. Routine experimentation may be performed to identify an optimal value of α. Finally, at step 270, a single preferred AP-VP delay value s selected from the pair candidate values as follows:

$$AP\text{-}VP = \text{MIN}(AP\text{-}VP_1, AP\text{-}VP_2).$$

It is believed that this value represents the optimal A-VP delay for achieving optimal cardiac performance at a base pacing rate. At the very least, it represents a preferred AP-VP delay for the base pacing rate. Alternatively, if desired, the external programmer may be programmed to simply select either the first candidate value or the second candidate value, or to average the values together. The various values may be presented to the physician who is then prompted to select one of the candidate values. The selected value of the AP-VP delay is transmitted to the implanted device, which uses the value to time delivery of ventricular pacing pulses following paced atrial events in accordance with otherwise conventional techniques.

Figure 6:
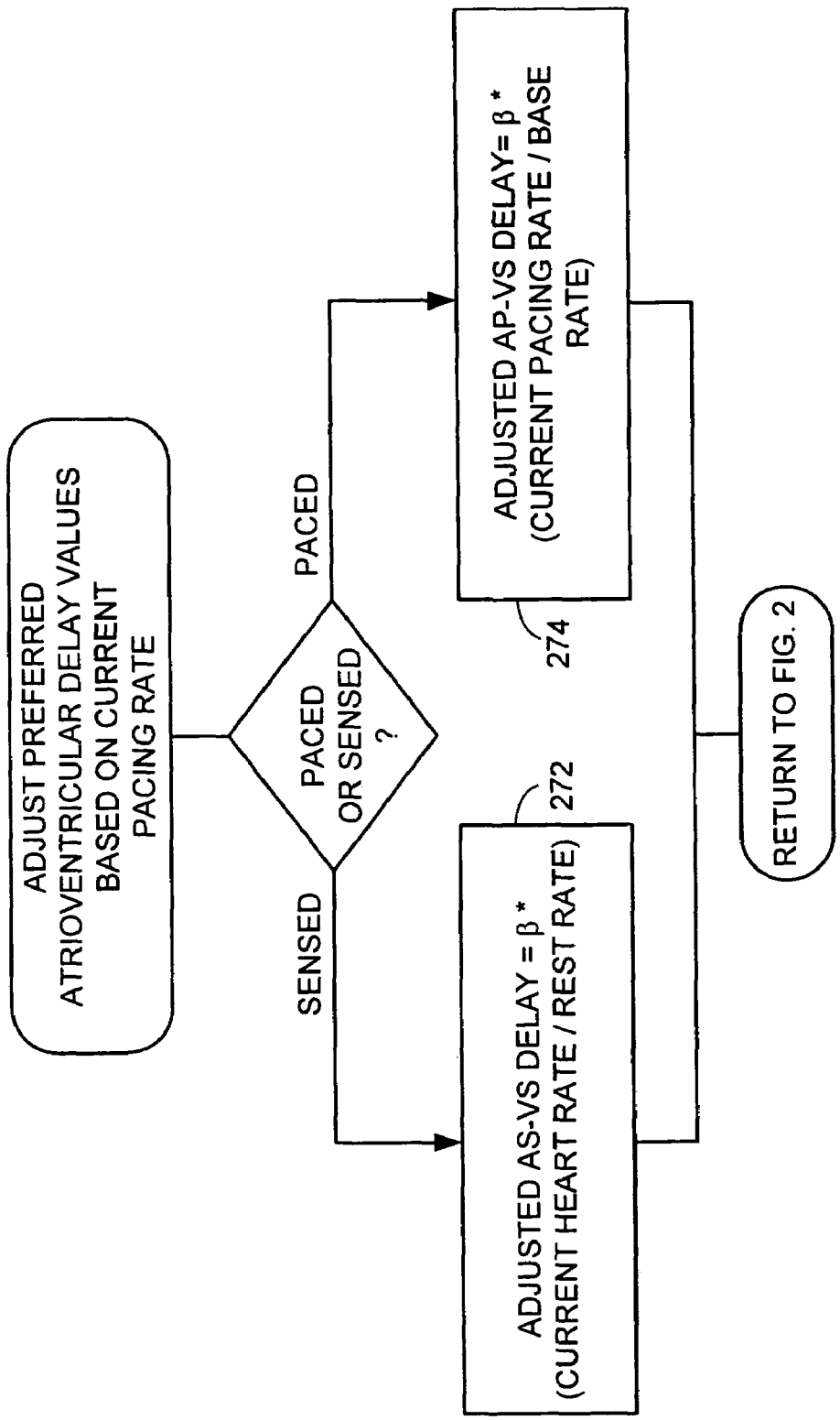
FIG. 6 is a flow chart illustrating an exemplary technique for adjusting optimal A-VP delay values based on heart rate or pacing rate for use with the technique of FIG. 2.

For pacing rates that are not at a base rate or for intrinsic rates that are not at a rest rate, the optimal AP-VP and AS-VP delay values are automatically adjusted by the implantable device using the technique FIG. 6. Again, the particular steps be performed depend upon whether atrial events are paced or sensed. For sensed events, step 272 is performed, wherein the AS-VP pacing delay value is adjusted as follows:

$$\text{Rate Adjusted } AS\text{-}VP = \beta^*(AS\text{-}VP)$$

where β=current heart rate/rest rate.

For paced events in atria, the AP-VP value is adjusted, at step 274, as follows:

$$\text{Rate Adjusted } AP\text{-}VP = \beta^*(AP\text{-}VP)$$

where β=current pacing rate/base rate.

Figure 7:
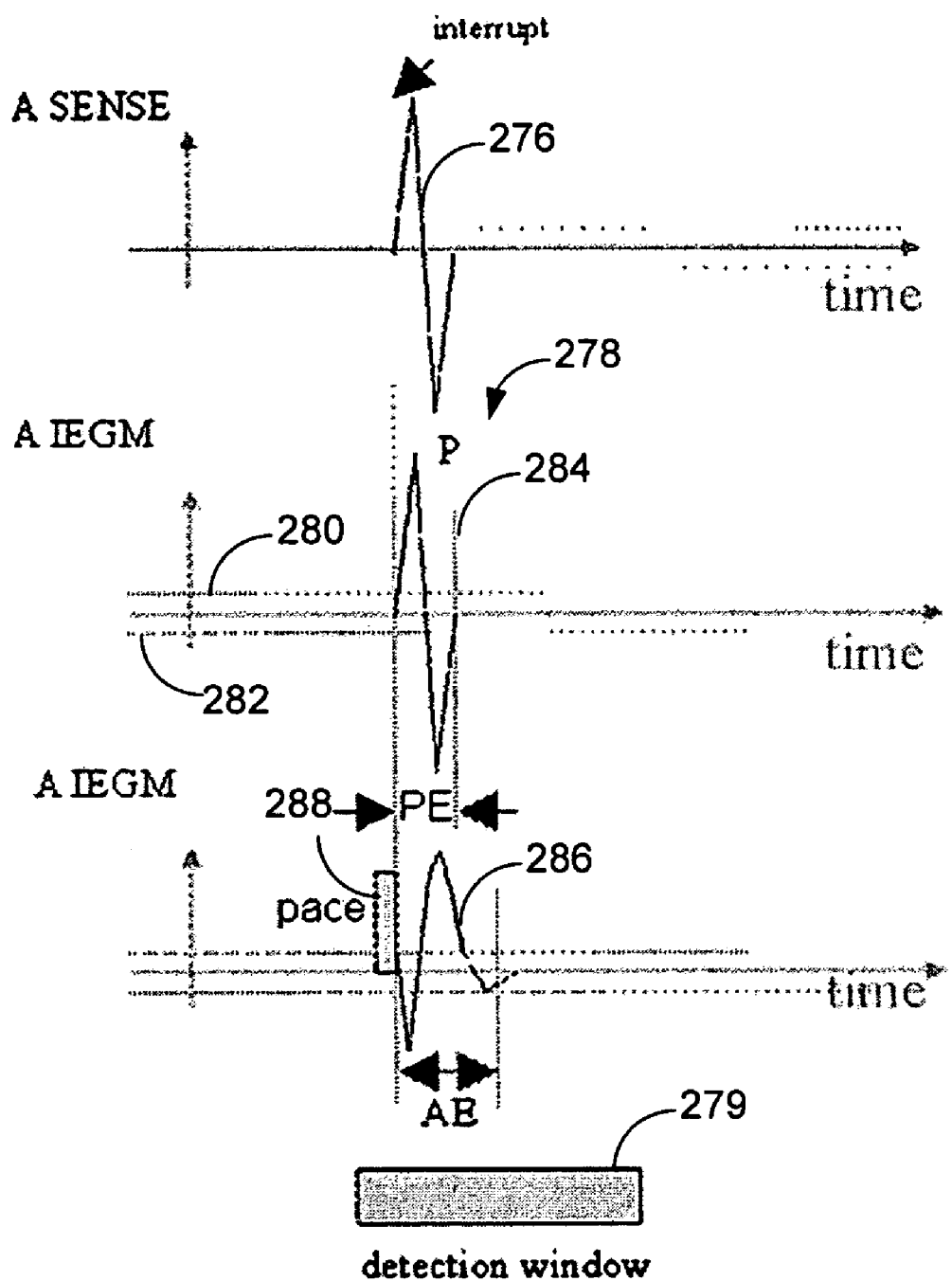
FIG. 7 is a graph illustrating an exemplary technique for detecting the end of an atrial event for use with the techniques of FIGS. 3-4.

Referring now to FIG. 7, a technique for detecting the end of atrial events (i.e. either atrial depolarizations or evoked responses) will briefly be described. This technique may be used, for example, at step 216 of FIG. 3 for identifying the end of an intrinsic atrial depolarization. The technique is also used at step 224 of FIG. 3 for determining the end of an evoked response. However, the technique FIG. 7 may be used in other circumstances, as needed.

Within a FIG. 7, an atrial depolarization 276 within an atrial sense channel signal is shown along with a corresponding A-IEGM signal 278. An interrupt is triggered upon detection of the onset of the atrial event. Once the interrupt occurs, a detection window 279 is opened on the A-IEGM channel, with low positive and negative threshold levels (280 and 282, respectively), which may be, e.g., set to 0.1 mV and −0.1 mV, respectively. The detection window may be, for example, 200 ms in duration. So long as the amplitude of the signal on the A-IEGM channel is greater than the positive threshold or is less than the negative threshold, the corresponding time value is recorded. This time value is overwritten each time of the signal is found to have exceeded threshold values. The last time value 284 during the detection window wherein the signal is outside the threshold values is identified as the end of the atrial depolarization event. Alternatively, rather than search forward through the detection window to identify the last point at which the signal is outside the threshold values, the device may instead search backwards through the window to find the same point. In any case, a similar technique is used to detect the end of an evoked response 286 following an atrial paced event 288. With a paced event, the detection window commences immediately upon delivery of the atrial pulse. Within the figure, only a single detection window is shown, though different windows having different start times and durations may be separately opened for paced and sensed events.

Optimization Technique for use without Surface EKG

Figure 8:
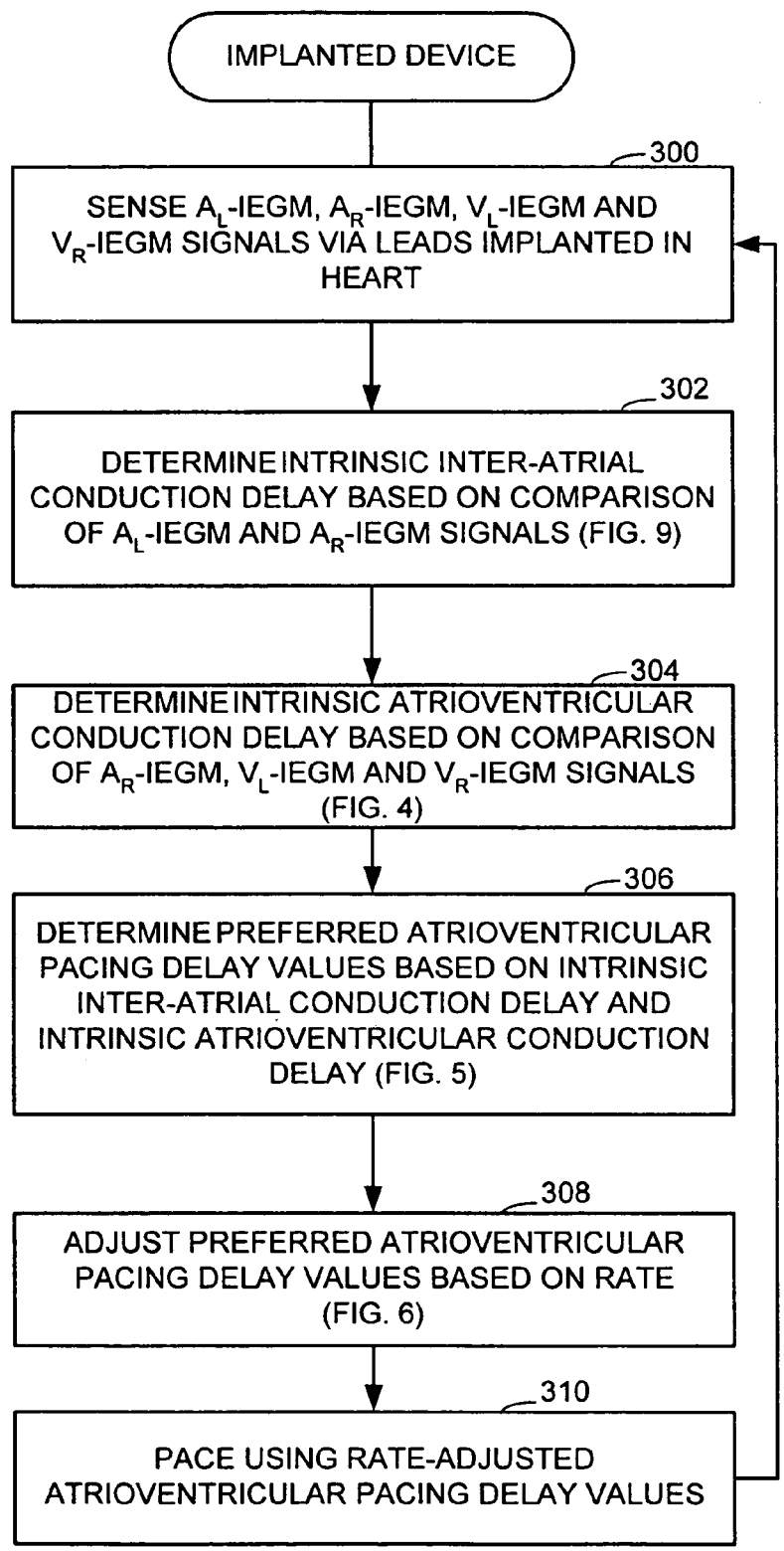
FIG. 8 is a flow chart illustrating an alternative exemplary technique for identifying optimal A-VP delay values in accordance with the general techniques of FIG. 1 but for use with an implantable device equipped to sense both left and right atrial IEGM signals.
Figure 9:
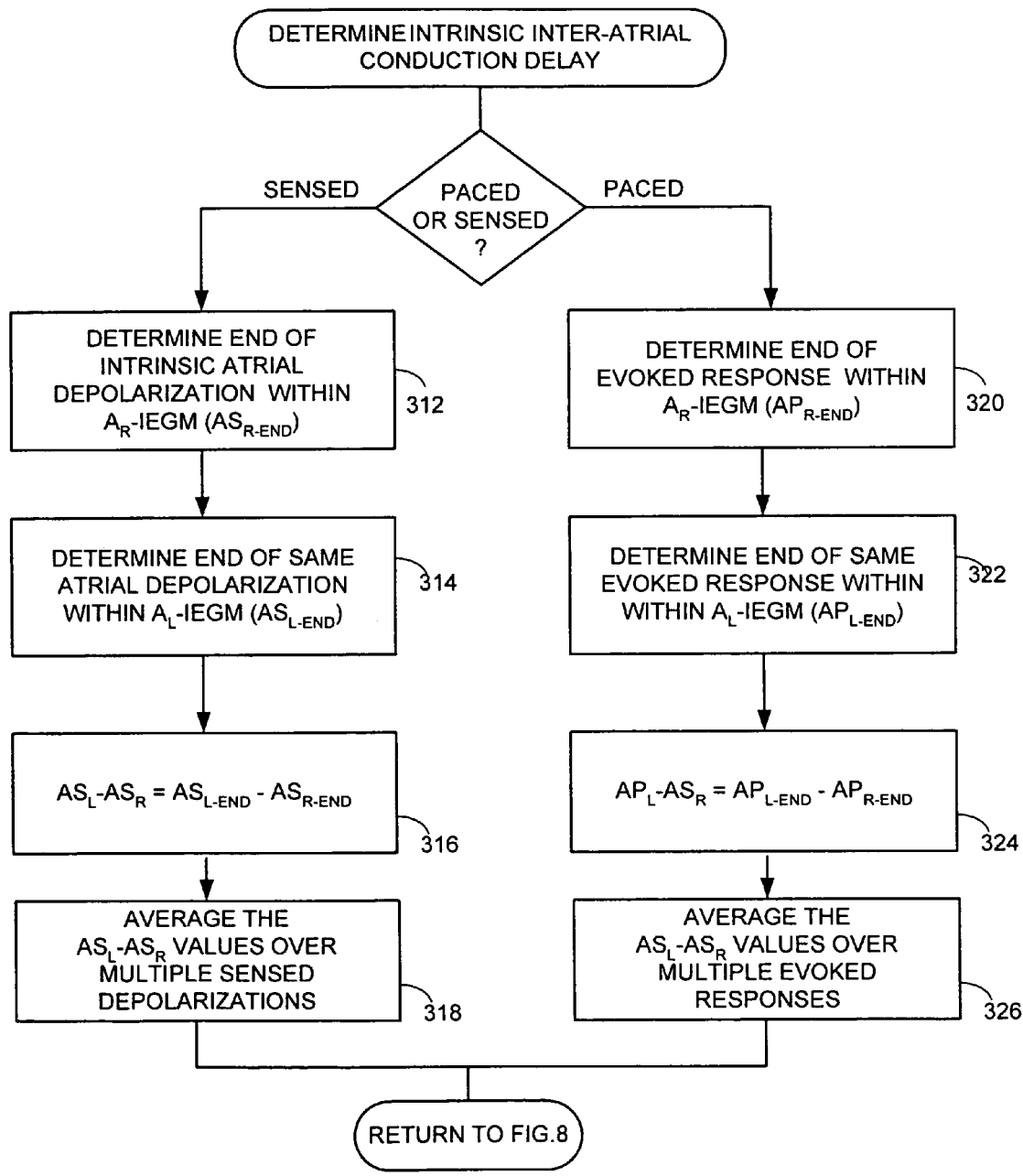
FIG. 9 is a flow chart illustrating an exemplary technique for determining intrinsic inter-atrial delay values based on left and aright atrial IEGM signals for use with the technique of FIG. 8.

What have been described thus far are techniques for determining preferred or optimal atrioventricular delay values for use with implantable systems not equipped to sense both left and right atrial IEGM signals. As explained, the inter-atrial delay is estimated based upon the width of atrial events sensed within the right atrium in combination with a correction value derived from the P-wave of the surface EKG. For systems that include a sensing electrode in the left atrium (such as systems employing CS leads), the inter-atrial delay may be more easily obtained simply by comparing signals sensed within the left and right atria. These techniques shall be described with reference to FIGS. 8-9. Many of the steps of FIGS. 8-9 are similar to those of figures FIGS. 2-7 and will not be described in detail. Whereas the techniques of FIGS. 2-7 are performed by an external programmer using signals received from the implanted device and from a surface EKG unit, the steps performed for the technique of FIGS. 8-9 may be performed entirely by the implanted device, since a surface EKG is not required.

Figure 10:
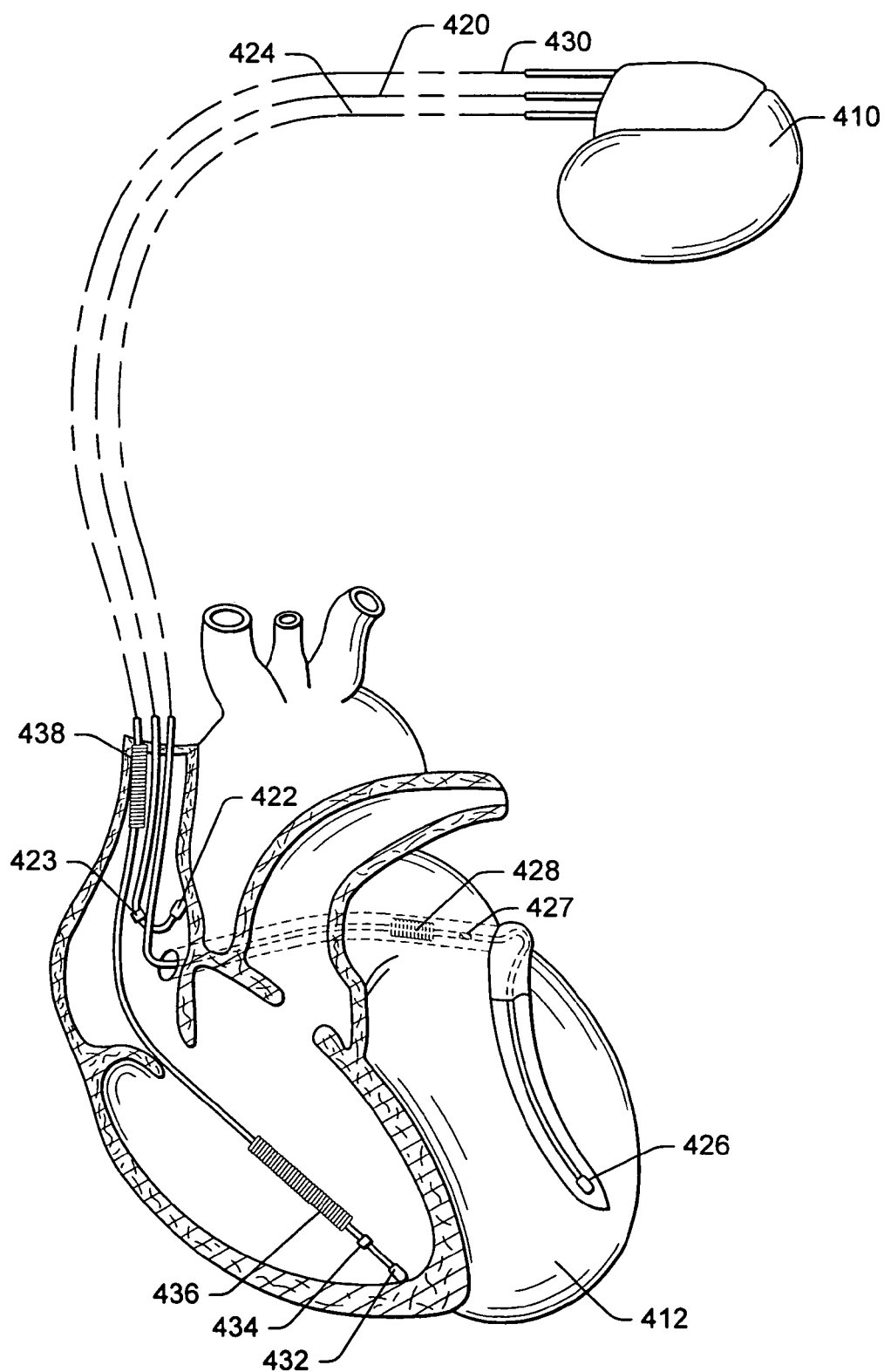
FIG. 10 is a simplified diagram illustrating an implantable stimulation device for use in implementing techniques of FIGS. 1-9.

Referring to FIG. 8, beginning at step 300, the implanted device senses left and right atrial and ventricular IEGM signals ($A_L$-IEGM, $A_R$-IEGM, $V_L$-IEGM, and $V_R$-IEGM) via leads implanted in the heart, with the $A_L$-IEGM signal sensed via electrodes in the left atrium, such as between left atrial ring electrode 427 and the device can of FIG. 10. (If electrode 427 is a bipolar electrode, then a separate return electrode is not required.) At step 302, the implanted device determines the intrinsic inter-atrial conduction delay by examining $A_L$-IEGM and $A_R$-IEGM signals, using a technique to be described below with reference to FIG. 9. At step 304, the implanted device determines the intrinsic atrioventricular conduction delay based upon a comparison of the $A_R$-IEGM signals and the left and right ventricular IEGM signals, using the technique already described above with reference to FIG. 4. At step 306, the device then determines preferred or optimal AS-VP and AP-VP delay values based on the intrinsic inter-atrial conduction delay and the intrinsic atrioventricular conduction delay, using the techniques already described above with reference to FIG. 5. As before, the preferred AS-VP and AP-VP delay values are adjusted based upon the current rate, at step 308, using the techniques of FIG. 6. Finally, at step 310, the device paces the ventricles of the patient using the rate-adjusted AS-VP and AP-VP delays.

Determination of the intrinsic inter-atrial conduction delay for use with a device equipped to sense both left and right atrial IEGM signals will now be described with reference to FIG. 9. As with the various techniques discussed above, processing depends upon whether atrial events are sensed or paced. Referring first to sensed events, beginning at step 312, the implanted device determines the end of an intrinsic atrial depolarization within the $A_R$-IEGM signal. The end of the intrinsic atrial depolarization as sensed within the right atrium is referred to herein as $AS_{R-END}$. At step 314, the implanted device then determines the end of the same atrial depolarization event within an $A_L$-IEGM signal. Herein, the end of the intrinsic atrial depolarization in the $A_L$-IEGM signal is referred to as $AS_{L-END}$. The techniques of FIG. 7 may be used to identify the ends of the atrial event within steps 312 and 314.

At step 316, the implanted device then calculates the intrinsic inter-atrial delay for the sensed atrial event using the following equation:

$$AS_L\text{-}AS_R = AS_{L-END} - AS_{R-END}.$$

At step 318, the device averages individual inter-atrial delays over multiple sensed depolarizations, preferably at least 10 to 20.

A similar sequence of steps is used in connection with paced events in the atria. Briefly, at step 320, the implanted device determines the end of an evoked response within the right atrium. Then, at step 322, device determines the end of the same evoked response within the left atrial IEGM. At step 324, device calculates the inter-atrial delay for the evoked response using the following equation:

$$AP_L\text{-}AS_R = AP_{L-END} - AP_{R-END}$$

At step 326, the device averages inter-atrial delay values for multiple paced events, again preferably at least 10 or 20.

Thus, upon completion of steps of FIG. 9, the device has calculated separate average intrinsic inter-atrial delay values for both sensed and paced atrial events, which are then used within the technique of FIG. 5 to determine optimal or preferred AS-VP and AP-VP delay values, as has already described.

What have been described thus far are various techniques for determining preferred or optimal AS-VP and AP-VP delay values for use by an implantable cardiac stimulation device. Depending upon the implementation, the determination techniques are performed by the implanted device itself or by an external programmer. For the sake of completeness, detailed descriptions of exemplary implantable cardiac stimulation devices and external programmers will now be described.

Exemplary Pacer/ICD

Figure 11:
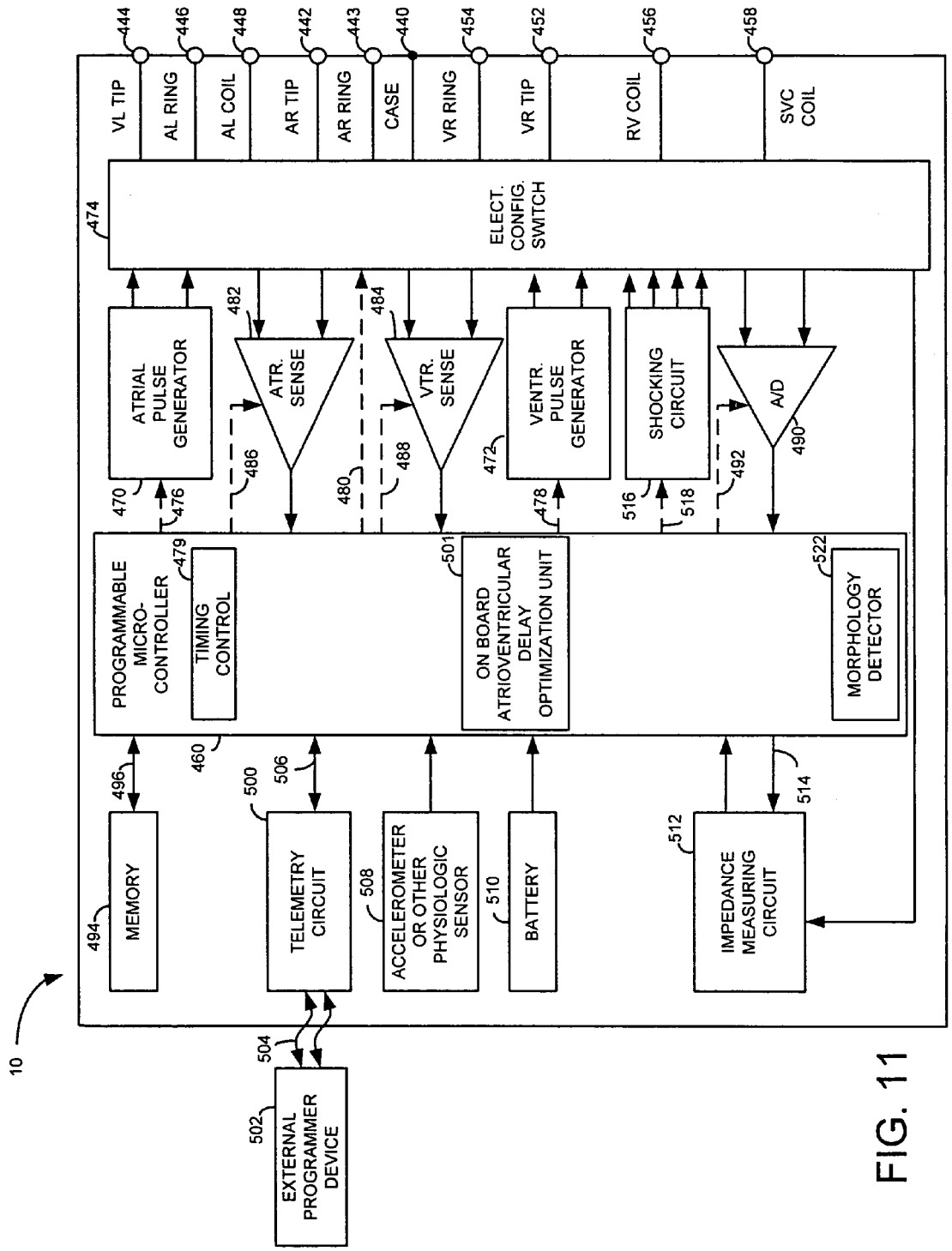
FIG. 11 is a functional block diagram of internal components of the implantable device of FIG. 11.
Figure 12:
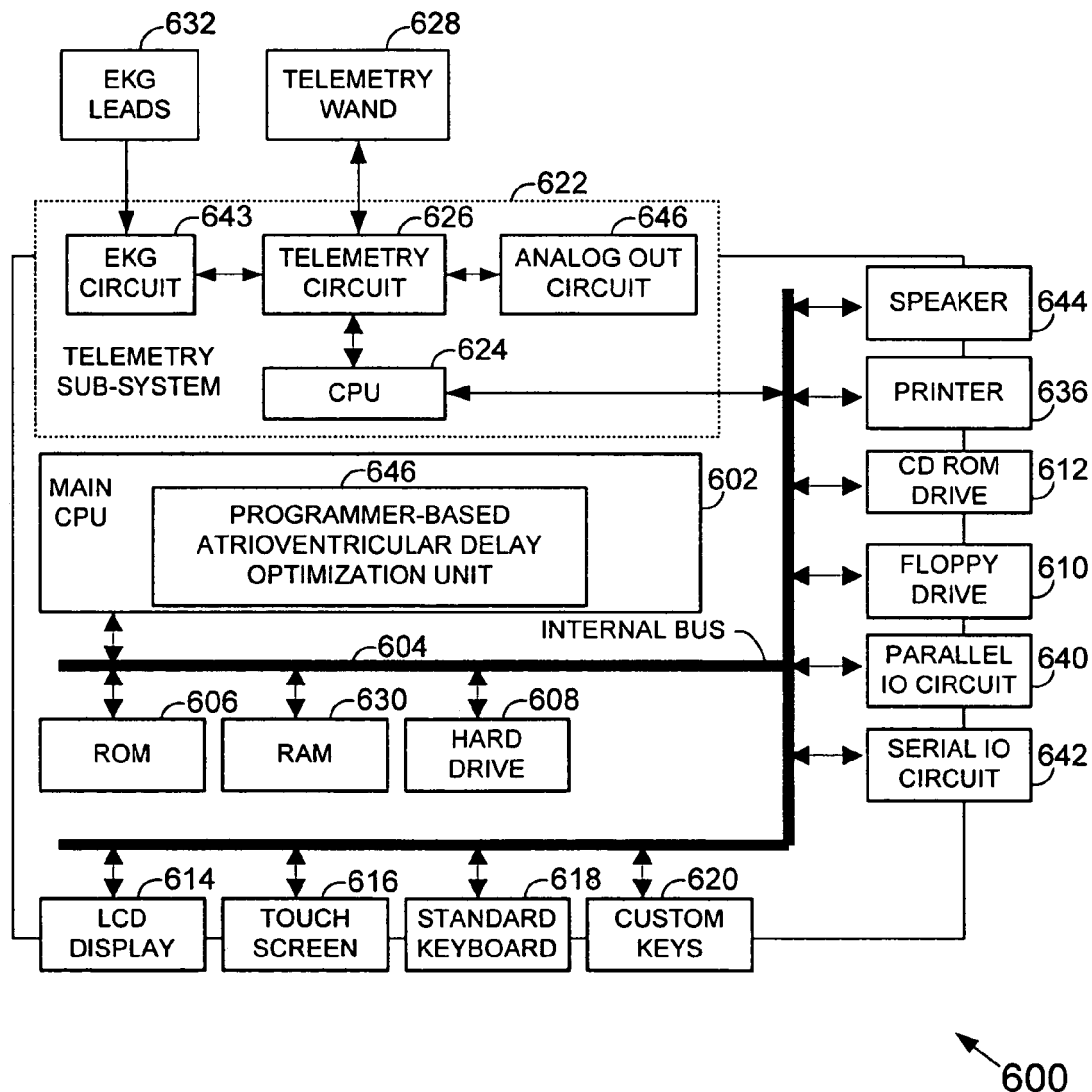
FIG. 12 is a functional block diagram of an external programmer device for use in implementing techniques of FIGS. 1-9.

With reference to FIGS. 10 and 11, a description of an exemplary pacer/ICD will now be provided. FIG. 10 provides a simplified block diagram of the pacer/ICD, which is a dual-chamber stimulation device capable of treating both fast and slow arrhythmias with stimulation therapy, including cardioversion, defibrillation, and pacing stimulation. To provide atrial chamber pacing stimulation and sensing, pacer/ICD 410 is shown in electrical communication with a heart 412 by way of a left atrial lead 420 having an atrial tip electrode 422 and an atrial ring electrode 423 implanted in the atrial appendage. Pacer/ICD 410 is also in electrical communication with the heart by way of a right ventricular lead 430 having, in this embodiment, a ventricular tip electrode 432, a right ventricular ring electrode 434, a right ventricular (RV) coil electrode 436, and a superior vena cava (SVC) coil electrode 438. Typically, the right ventricular lead 430 is transvenously inserted into the heart so as to place the RV coil electrode 436 in the right ventricular apex, and the SVC coil electrode 438 in the superior vena cava. Accordingly, the right ventricular lead is capable of receiving cardiac signals, and delivering stimulation in the form of pacing and shock therapy to the right ventricle.

To sense left atrial and ventricular cardiac signals and to provide left chamber pacing therapy, pacer/ICD 410 is coupled to a CS lead 424 designed for placement in the "CS region" via the CS os for positioning a distal electrode adjacent to the left ventricle and/or additional electrode(s) adjacent to the left atrium. As used herein, the phrase "CS region" refers to the venous vasculature of the left ventricle, including any portion of the CS, great cardiac vein, left marginal vein, left posterior ventricular vein, middle cardiac vein, and/or small cardiac vein or any other cardiac vein accessible by the CS. Accordingly, an exemplary CS lead 424 is designed to receive atrial and ventricular cardiac signals and to deliver left ventricular pacing therapy using at least a left ventricular tip electrode 426, left atrial pacing therapy using at least a left atrial ring electrode 427, and shocking therapy using at least a left atrial coil electrode 428. With this configuration, biventricular pacing can be performed. Although only three leads are shown in FIG. 10, it should also be understood that additional stimulation leads (with one or more pacing, sensing and/or shocking electrodes) may be used in order to efficiently and effectively provide pacing stimulation to the left side of the heart or atrial cardioversion and/or defibrillation.

A simplified block diagram of internal components of pacer/ICD 410 is shown in FIG. 11. While a particular pacer/ICD is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation as well as providing for the aforementioned apnea detection and therapy.

The housing 440 for pacer/ICD 410, shown schematically in FIG. 11, is often referred to as the "can", "case" or "case electrode" and may be programmably selected to act as the return electrode for all "unipolar" modes. The housing 440 may further be used as a return electrode alone or in combination with one or more of the coil electrodes, 428, 436 and 438, for shocking purposes. The housing 440 further includes a connector (not shown) having a plurality of terminals, 442, 443, 444, 446, 448, 452, 454, 456 and 458 (shown schematically and, for convenience, the names of the electrodes to which they are connected are shown next to the terminals). As such, to achieve right atrial sensing and pacing, the connector includes at least a right atrial tip terminal (AR TIP) 442 adapted for connection to the atrial tip electrode 422 and a right atrial ring ($A_R$ RING) electrode 443 adapted for connection to right atrial ring electrode 423. To achieve left chamber sensing, pacing and shocking, the connector includes at least a left ventricular tip terminal ($V_L$ TIP) 444, a left atrial ring terminal ($A_L$ RING) 446, and a left atrial shocking terminal ($A_L$ COIL) 448, which are adapted for connection to the left ventricular ring electrode 426, the left atrial ring electrode 427, and the left atrial coil electrode 428, respectively. To support right chamber sensing, pacing and shocking, the connector further includes a right ventricular tip terminal ($V_R$ TIP) 452, a right ventricular ring terminal ($V_R$ RING) 454, a right ventricular shocking terminal ($V_R$ COIL) 456, and an SVC shocking terminal (SVC COIL) 458, which are adapted for connection to the right ventricular tip electrode 432, right ventricular ring electrode 434, the $V_R$ coil electrode 436, and the SVC coil electrode 438, respectively.

At the core of pacer/ICD 410 is a programmable microcontroller 460, which controls the various modes of stimulation therapy. As is well known in the art, the microcontroller 460 (also referred to herein as a control unit) typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 460 includes the ability to process or monitor input signals (data) as controlled by a program code stored in a designated block of memory. The details of the design and operation of the microcontroller 460 are not critical to the invention. Rather, any suitable microcontroller 460 may be used that carries out the functions described herein. The use of microprocessor-based control circuits for performing timing and data analysis functions are well known in the art.

As shown in FIG. 11, an atrial pulse generator 470 and a ventricular pulse generator 472 generate pacing stimulation pulses for delivery by the right atrial lead 420, the right ventricular lead 430, and/or the CS lead 424 via an electrode configuration switch 474. It is understood that in order to provide stimulation therapy in each of the four chambers of the heart, the atrial and ventricular pulse generators, 470 and 472, may include dedicated, independent pulse generators, multiplexed pulse generators or shared pulse generators. The pulse generators, 470 and 472, are controlled by the microcontroller 460 via appropriate control signals, 476 and 478, respectively, to trigger or inhibit the stimulation pulses.

The microcontroller 460 further includes timing control circuitry (not separately shown) used to control the timing of such stimulation pulses (e.g., pacing rate, atrioventricular delay, atrial interconduction (inter-atrial) delay, or ventricular interconduction (V-V) delay, etc.) as well as to keep track of the timing of refractory periods, blanking intervals, noise detection windows, evoked response windows, alert intervals, marker channel timing, etc., which is well known in the art. Switch 474 includes a plurality of switches for connecting the desired electrodes to the appropriate I/O circuits, thereby providing complete electrode programmability. Accordingly, the switch 474, in response to a control signal 480 from the microcontroller 460, determines the polarity of the stimulation pulses (e.g., unipolar, bipolar, combipolar, etc.) by selectively closing the appropriate combination of switches (not shown) as is known in the art. Moreover, as the explained in greater detail below, the microcontroller transmits signals to controlling the switch to connect a different set of electrodes during a far-field overdrive pacing than during near-field overdrive pacing.

Atrial sensing circuits 482 and ventricular sensing circuits 484 may also be selectively coupled to the right atrial lead 420, CS lead 424, and the right ventricular lead 430, through the switch 474 for detecting the presence of cardiac activity in each of the four chambers of the heart. Accordingly, the atrial (ATR. SENSE) and ventricular (VTR. SENSE) sensing circuits, 482 and 484, may include dedicated sense amplifiers, multiplexed amplifiers or shared amplifiers. The switch 474 determines the "sensing polarity" of the cardiac signal by selectively closing the appropriate switches, as is also known in the art. In this way, the clinician may program the sensing polarity independent of the stimulation polarity. Each sensing circuit, 482 and 484, preferably employs one or more low power, precision amplifiers with programmable gain and/or automatic gain control, bandpass filtering, and a threshold detection circuit, as known in the art, to selectively sense the cardiac signal of interest. The automatic gain control enables pacer/ICD 410 to deal effectively with the difficult problem of sensing the low amplitude signal characteristics of atrial or ventricular fibrillation. The outputs of the atrial and ventricular sensing circuits, 482 and 484, are connected to the microcontroller 460 which, in turn, are able to trigger or inhibit the atrial and ventricular pulse generators, 470 and 472, respectively, in a demand fashion in response to the absence or presence of cardiac activity in the appropriate chambers of the heart.

For arrhythmia detection, pacer/ICD 410 utilizes the atrial and ventricular sensing circuits, 482 and 484, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 460 by comparing them to a predefined rate zone limit (i.e., bradycardia, normal, atrial tachycardia, atrial fibrillation, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, antitachycardia pacing, cardioversion shocks or defibrillation shocks).

Cardiac signals are also applied to the inputs of an analog-to-digital (A/D) data acquisition system 490. The data acquisition system 490 is configured to acquire intracardiac electrogram signals, convert the raw analog data into a digital signal, and store the digital signals for later processing and/or telemetric transmission to an external device 502. The data acquisition system 490 is coupled to the right atrial lead 420, the CS lead 424, and the right ventricular lead 430 through the switch 474 to sample cardiac signals across any pair of desired electrodes. The microcontroller 460 is further coupled to a memory 494 by a suitable data/address bus 496, wherein the programmable operating parameters used by the microcontroller 460 are stored and modified, as required, in order to customize the operation of pacer/ICD 410 to suit the needs of a particular patient. Such operating parameters define, for example, pacing pulse amplitude or magnitude, pulse duration, electrode polarity, rate, sensitivity, automatic features, arrhythmia detection criteria, and the amplitude, waveshape and vector of each shocking pulse to be delivered to the patient's heart within each respective tier of therapy. Other pacing parameters include base rate, rest rate and circadian base rate.

Advantageously, the operating parameters of the implantable pacer/ICD 410 may be non-invasively programmed into the memory 494 through a telemetry circuit 500 in telemetric communication with the external device 502, such as a programmer, transtelephonic transceiver or a diagnostic system analyzer. The telemetry circuit 500 is activated by the microcontroller by a control signal 506. The telemetry circuit 500 advantageously allows intracardiac electrograms and status information relating to the operation of pacer/ICD 410 (as contained in the microcontroller 460 or memory 494) to be sent to the external device 502 through an established communication link 504. Pacer/ICD 410 further includes an accelerometer or other physiologic sensor 508, commonly referred to as a "rate-responsive" sensor because it is typically used to adjust pacing stimulation rate according to the exercise state of the patient. However, the physiological sensor 508 may further be used to detect changes in cardiac output, changes in the physiological condition of the heart, or diurnal changes in activity (e.g., detecting sleep and wake states) and to detect arousal from sleep. Accordingly, the microcontroller 460 responds by adjusting the various pacing parameters (such as rate, AS-VP delay, AP-VP delay, V-V delay, etc.) at which the atrial and ventricular pulse generators, 470 and 472, generate stimulation pulses. While shown as being included within pacer/ICD 410, it is to be understood that the physiologic sensor 508 may also be external to pacer/ICD 410, yet still be implanted within or carried by the patient. A common type of rate responsive sensor is an activity sensor incorporating an accelerometer or a piezoelectric crystal, which is mounted within the housing 440 of pacer/ICD 410. Other types of physiologic sensors are also known, for example, sensors that sense the oxygen content of blood, respiration rate and/or minute ventilation, pH of blood, ventricular gradient, etc.

Insofar as atrioventricular delay values are concerned, the microcontroller includes an on-board A-VP delay optimization unit 501, which operates in accordance with techniques of FIGS. 8 and 9 to determine preferred or optimal AS-VP and AP-VP delay values based on IEGM signals. If the device is not coupled to a CS lead or other lead capable of sensing in the left atria, the optimization unit 501 is deactivated and optimization of AS-VP and AP-VP is instead performed by an external programmer.

The pacer/ICD additionally includes a battery 510, which provides operating power to all of the circuits shown in FIG. 11. The battery 510 may vary depending on the capabilities of pacer/ICD 410. If the system only provides low voltage therapy, a lithium iodine or lithium copper fluoride cell may be utilized. For pacer/ICD 410, which employs shocking therapy, the battery 510 must be capable of operating at low current drains for long periods, and then be capable of providing high-current pulses (for capacitor charging) when the patient requires a shock pulse. The battery 510 must also have a predictable discharge characteristic so that elective replacement time can be detected. Accordingly, pacer/ICD 410 is preferably capable of high voltage therapy and appropriate batteries.

As further shown in FIG. 11, pacer/ICD 410 is shown as having an impedance measuring circuit 512 which is enabled by the microcontroller 460 via a control signal 514. Herein, thoracic impedance is primarily detected for use in tracking thoracic respiratory oscillations. Other uses for an impedance measuring circuit include, but are not limited to, lead impedance surveillance during the acute and chronic phases for proper lead positioning or dislodgement; detecting operable electrodes and automatically switching to an operable pair if dislodgement occurs; measuring respiration or minute ventilation; measuring thoracic impedance for determining shock thresholds; detecting when the device has been implanted; measuring respiration; and detecting the opening of heart valves, etc. The impedance measuring circuit 120 is advantageously coupled to the switch 74 so that any desired electrode may be used.

In the case where pacer/ICD 410 is intended to operate as an implantable cardioverter/defibrillator (ICD) device, it detects the occurrence of an arrhythmia, and automatically applies an appropriate electrical shock therapy to the heart aimed at terminating the detected arrhythmia. To this end, the microcontroller 460 further controls a shocking circuit 516 by way of a control signal 518. The shocking circuit 516 generates shocking pulses of low (up to 0.5 joules), moderate (0.5-10 joules) or high energy (11 to 40 joules), as controlled by the microcontroller 460. Such shocking pulses are applied to the heart of the patient through at least two shocking electrodes, and as shown in this embodiment, selected from the left atrial coil electrode 428, the RV coil electrode 436, and/or the SVC coil electrode 438. The housing 440 may act as an active electrode in combination with the RV electrode 436, or as part of a split electrical vector using the SVC coil electrode 438 or the left atrial coil electrode 428 (i.e., using the RV electrode as a common electrode). Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 460 is capable of controlling the synchronous or asynchronous delivery of the shocking pulses.

In addition, the stimulation device may be configured to perform Automatic Mode Switching (AMS) wherein the pacemaker reverts from a tracking mode such as a VDD or DDD mode to a nontracking mode such as VVI or DDI mode. VDD, DDD, VVI and DDI are standard device codes that identify the mode of operation of the device. DDD indicates a device that senses and paces in both the atria and the ventricles and is capable of both triggering and inhibiting functions based upon events sensed in the atria and the ventricles. VDD indicates a device that sensed in both the atria and ventricles but only paces in the ventricles. A sensed event on the atrial channel triggers ventricular outputs after a programmable delay, the pacemaker's equivalent of a PR interval. VVI indicates that the device is capable of pacing and sensing only in the ventricles and is only capable of inhibiting the functions based upon events sensed in the ventricles. DDI is identical to DDD except that the device is only capable of inhibiting functions based upon sensed events, rather than triggering functions. As such, the DDI mode is a non-tracking mode precluding its triggering ventricular outputs in response to sensed atrial events. Numerous other device modes of operation are possible, each represented by standard abbreviations of this type.

Overview of Exemplary External Programmer

FIG. 12 illustrates pertinent components of an external programmer for use in programming an implantable medical device such as a pacemaker or ICD. Briefly, the programmer permits a physician or other user to program the operation of the implanted device and to retrieve and display information received from the implanted device such as IEGM data and device diagnostic data. Additionally, the external programmer receives and displays EKG data from separate external EKG leads that may be attached to the patient. Depending upon the specific programming of the external programmer, programmer 600 may also be capable of processing and analyzing data received from the implanted device and from the EKG leads to, for example, render preliminary diagnosis as to medical conditions of the patient or to the operations of the implanted device. As noted, the programmer is also configured to determination preferred or optimal AS-VP and AP-VP delay values.

Now, considering the components of programmer 600, operations of the programmer are controlled by a CPU 602, which may be a generally programmable microprocessor or microcontroller or may be a dedicated processing device such as an application specific integrated circuit (ASIC) or the like. Software instructions to be performed by the CPU are accessed via an internal bus 604 from a read only memory (ROM) 606 and random access memory 630. Additional software may be accessed from a hard drive 608, floppy drive 610, and CD ROM drive 612, or other suitable permanent mass storage device. Depending upon the specific implementation, a basic input output system (BIOS) is retrieved from the ROM by CPU at power up. Based upon instructions provided in the BIOS, the CPU "boots up" the overall system in accordance with well-established computer processing techniques.

Once operating, the CPU displays a menu of programming options to the user via an LCD display 614 or other suitable computer display device. To this end, the CPU may, for example, display a menu of specific programming parameters of the implanted device to be programmed or may display a menu of types of diagnostic data to be retrieved and displayed. In response thereto, the physician enters various commands via either a touch screen 616 overlaid on the LCD display or through a standard keyboard 618 supplemented by additional custom keys 620, such as an emergency VVI (EVVI) key. The EVVI key sets the implanted device to a safe VVI mode with high pacing outputs. This ensures life sustaining pacing operation in nearly all situations but by no means is it desirable to leave the implantable device in the EVVI mode at all times.

Once all pacing leads are mounted and the pacing device is implanted, the various devices are programmed. Typically, the physician initially controls the programmer 600 to retrieve data stored within any implanted devices and to also retrieve EKG data from EKG leads, if any, coupled to the patient. To this end, CPU 602 transmits appropriate signals to a telemetry subsystem 622, which provides components for directly interfacing with the implanted devices, and the EKG leads. Telemetry subsystem 622 includes its own separate CPU 624 for coordinating the operations of the telemetry subsystem. Main CPU 602 of programmer communicates with telemetry subsystem CPU 624 via internal bus 604. Telemetry subsystem additionally includes a telemetry circuit 626 connected to telemetry wand 628, which, in turn, receives and transmits signals electromagnetically from a telemetry unit of the implanted device. The telemetry wand is placed over the chest of the patient near the implanted device to permit reliable transmission of data between the telemetry wand and the implanted device.

Typically, at the beginning of the programming session, the external programming device controls the implanted devices via appropriate signals generated by the telemetry wand to output all previously recorded patient and device diagnostic information. Patient diagnostic information includes, for example, recorded IEGM data and statistical patient data such as the percentage of paced versus sensed heartbeats. Device diagnostic data includes, for example, information representative of the operation of the implanted device such as lead impedances, battery voltages, battery recommended replacement time (RRT) information and the like. Data retrieved from the implanted devices is stored by external programmer 600 either within a random access memory (RAM) 630, hard drive 608 or within a floppy diskette placed within floppy drive 610. Additionally, or in the alternative, data may be permanently or semi-permanently stored within a compact disk (CD) or other digital media disk, if the overall system is configured with a drive for recording data onto digital media disks, such as a write once read many (WORM) drive.

Once all patient and device diagnostic data previously stored within the implanted devices is transferred to programmer 600, the implanted devices may be further controlled to transmit additional data in real time as it is detected by the implanted devices, such as additional IEGM data, lead impedance data, and the like. Additionally, or in the alternative, telemetry subsystem 622 receives EKG signals from EKG leads 632 via an EKG processing circuit 634. As with data retrieved from the implanted device itself, signals received from the EKG leads are stored within one or more of the storage devices of the external programmer. Typically, EKG leads output analog electrical signals representative of the EKG. Accordingly, EKG circuit 634 includes analog to digital conversion circuitry for converting the signals to digital data appropriate for further processing within programmer. Depending upon the implementation, the EKG circuit may be configured to convert the analog signals into event record data for ease of processing along with the event record data retrieved from the implanted device. Typically, signals received from the EKG leads are received and processed in real time.

Thus, the programmer receives data both from the implanted devices and from the external EKG leads. Data retrieved from the implanted devices includes parameters representative of the current programming state of the implanted devices. Under the control of the physician, the external programmer displays the current programming parameters and permits the physician to reprogram the parameters. To this end, the physician enters appropriate commands via any of the aforementioned input devices and, under control of CPU 602, the programming commands are converted to specific programming parameters for transmission to the implanted devices via telemetry wand 628 to thereby reprogram the implanted devices. Prior to reprogramming specific parameters, the physician may control the external programmer to display any or all of the data retrieved from the implanted devices or from the EKG leads, including displays of ECGs, IEGMs, and statistical patient information. Any or all of the information displayed by programmer may also be printed using a printer 636.

A wide variety of parameters may be programmed by the physician. Insofar as AS-VP and AP-VP delay values are concerned, the microcontroller includes a programmer-based A-VP delay optimization unit 646, which operates in accordance with technique of FIGS. 2-7 to determine preferred or optimal AS-VP and AP-VP delay values based on surface EKG signals and IEGM signals received from an implanted device. Additionally V-V delays of the implanted device may be adjusted to further optimize cardiac function. In one example, the $V_R$-$V_L$ delay is first set to zero while the AS-VP and AP-VP delays are adjusted to achieve the best possible cardiac function (measured using any appropriate cardiac function measurement technique). Then, the $V_R$-$V_L$ delay is adjusted to achieve still further enhancements in cardiac function. With atrioventricular and inter-ventricular delay values optimized, it is believed that the best possible cardiac function can be achieved for the patient.

Programmer 600 also includes a modem 638 to permit direct transmission of data to other programmers via the public switched telephone network (PSTN) or other interconnection line, such as a T1 line or fiber optic cable. Depending upon the implementation, the modem may be connected directly to internal bus 604 may be connected to the internal bus via either a parallel port 640 or a serial port 642. Other peripheral devices may be connected to the external programmer via parallel port 640 or a serial port 642 as well. Although one of each is shown, a plurality of input output (IO) ports might be provided. A speaker 644 is included for providing audible tones to the user, such as a warning beep in the event improper input is provided by the physician. Telemetry subsystem 622 additionally includes an analog output circuit 646 for controlling the transmission of analog output signals, such as IEGM signals output to an EKG machine or chart recorder.

With the programmer configured as shown, a physician or other user operating the external programmer is capable of retrieving, processing and displaying a wide range of information received from the EKG leads or from the implanted devices and to reprogram the implanted devices if needed. The descriptions provided herein with respect to FIG. 11 are intended merely to provide an overview of the operation of programmer and are not intended to describe in detail every feature of the hardware and software of the device and is not intended to provide an exhaustive list of the functions performed by the device.

In general, while the invention has been described with reference to particular embodiments, modifications can be made thereto without departing from the spirit and scope of the invention. Note also that the term "including" as used herein is intended to be inclusive, i.e. "including but not limited to."

What is claimed is:

1. A method for determining an atrioventricular delay value for use in delivering cardiac pacing therapy to a heart of a patient in which an implantable cardiac stimulation device is implanted, the method comprising:
   determining an inter-atrial conduction delay for the patient;
   determining an intrinsic atrioventricular conduction delay for the patient; and
   determining an atrioventricular delay value for use in pacing based on the inter-atrial conduction delay and the intrinsic atrioventricular conduction delay;
   wherein determining the inter-atrial conduction delay for the patient comprises:
   determining a width of an electrical atrial event; and
   deriving the inter-atrial conduction delay from the width of the atrial event;
   wherein determining the width of the atrial event comprises:
   inputting an atrial intracardiac electrogram (A-IEGM) signal derived from a lead implanted within the atria of the patient;
   inputting a surface electrocardiogram (EKG) signal derived from leads mounted externally on the patient;
   determining a value representative of the duration of an atrial event detected within the A-IEGM signal; and
   adjusting the value based on a comparison of the A-IEGM signal and the EKG signal.

2. A method for determining an atrioventricular delay value for use in delivering cardiac pacing therapy to a heart of a patient in which an implantable cardiac stimulation device is implanted, the method comprising:
   determining an inter-atrial conduction delay for the patient;
   determining an intrinsic atrioventricular conduction delay for the patient; and
   determining an atrioventricular delay value for use in pacing based on the inter-atrial conduction delay and the intrinsic atrioventricular conduction delay;
   wherein determining the atrioventricular delay value based on the inter-atrial conduction delay and the intrinsic atrioventricular conduction delay comprises:
   determining a first candidate delay value (AS-VP$_1$) based on the inter-atrial conduction delay in combination with the intrinsic atrioventricular delay derived from sensed atrial events;
   determining a second candidate delay value (AS-VP$_2$) based on the inter-atrial conduction delay derived from sensed atrial events; and
   evaluating a AS-VP delay based on a comparison of AS-VP$_1$ and AS-VP$_2$.

3. The method of claim 2 further comprising delivering pacing therapy using the implantable cardiac stimulation device subject to the atrioventricular delay value.

4. The method of claim 2 wherein determining the inter-atrial conduction delay for the patient comprises:
   determining a width of an electrical atrial event; and
   deriving the inter-atrial conduction delay from the width of the atrial event.

5. The method of claim 4 wherein the atrial event is representative of an intrinsic atrial depolarization.

6. The method of claim 2 wherein evaluating the AS-VP delay based on a comparison of AS-VP$_1$ and AS-VP$_2$ is performed by selecting the shorter of the AS-VP$_1$, AS-VP$_2$ values.

7. The method of claim 2 wherein determining the atrioventricular delay value is performed by the implanted device based on intracardiac electrogram (IEGM) signals.

8. The method of claim 2 further comprising adjusting the atrioventricular delay value based on current patient heart rate.

9. The method of claim 8 wherein adjusting the atrioventricular delay value based on patient heart rate is performed by applying a scaling factor ($\beta$) to a delay value between a sensed atrial event and a subsequent paced ventricular event (AS-VP) wherein the scaling factor is based on current heart rate or a resting heart rate.

10. A method for determining an atrioventricular delay value for use in delivering cardiac pacing therapy to a heart of a patient in which an implantable cardiac stimulation device is implanted, the method comprising:
- determining an inter-atrial conduction delay for the patient;
- determining an intrinsic atrioventricular conduction delay for the patient; and
- determining an atrioventricular delay value for use in pacing based on the inter-atrial conduction delay and the intrinsic atrioventricular conduction delay;
- wherein determining atrioventricular pacing delay values based on the inter-atrial conduction delay and the intrinsic atrioventricular conduction delay comprises:
  - determining a first candidate delay value ($AP\text{-}VP_1$) based on the inter-atrial conduction delay in combination with the intrinsic atrioventricular delay derived from paced atrial events;
  - determining a second candidate delay value ($AP\text{-}VP_2$) based on the inter-atrial conduction delay derived from paced atrial events; and
  - evaluating a AP-VP delay based on a comparison of $AP\text{-}VP_1$ and $AP\text{-}VP_2$.

11. The method of claim 10 wherein the atrial event is representative of an atrial evoked response.

12. A method for determining an atrioventricular delay value for use in delivering cardiac pacing therapy to a heart of a patient in which an implantable cardiac stimulation device is implanted, the method comprising:
- determining an inter-atrial conduction delay for the patient;
- determining an intrinsic atrioventricular conduction delay for the patient; and
- determining an atrioventricular delay value for use in pacing based on the inter-atrial conduction delay and the intrinsic atrioventricular conduction delay;
- wherein determining an inter-atrial conduction delay for the patient comprises detecting the end of at least one atrial event in an atrial intracardiac electrogram (A-IEGM) signal by:
- detecting the onset of the atrial event in the A-IEGM signal;
- opening a detection window within the A-IEGM signal;
- setting positive and negative threshold values;
- identifying a last point in time within the detection window at which the A-IEGM signal falls outside the threshold values; and
- identifying the last point in time as being the end of the atrial event.

* * * * *